US011664033B2

(12) United States Patent
Jain et al.

(10) Patent No.: US 11,664,033 B2
(45) Date of Patent: May 30, 2023

(54) ELECTRONIC APPARATUS AND CONTROLLING METHOD THEREOF

(71) Applicant: SAMSUNG ELECTRONICS CO., LTD., Suwon-si (KR)

(72) Inventors: Maneesh Jain, Noida (IN); Arun Kumar Singh, Noida (IN); Atul Kumar Rai, Noida (IN)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

(21) Appl. No.: 17/158,669

(22) Filed: Jan. 26, 2021

(65) Prior Publication Data

US 2021/0390959 A1    Dec. 16, 2021

(30) Foreign Application Priority Data

Jun. 15, 2020  (IN) .............................. 202011024998
Oct. 15, 2020  (KR) ........................ 10-2020-0133183

(51) Int. Cl.
*G10L 17/06* (2013.01)
*G10L 17/04* (2013.01)
(Continued)

(52) U.S. Cl.
CPC ............ *G10L 17/06* (2013.01); *A61B 5/4803* (2013.01); *G10L 17/04* (2013.01); *G10L 17/20* (2013.01);
(Continued)

(58) Field of Classification Search
CPC ......... G10L 17/06; G10L 17/04; G10L 17/20; G10L 17/22; G10L 25/63; G10L 25/66; A61B 5/4803
(Continued)

(56) References Cited

U.S. PATENT DOCUMENTS 6,671,669 B1 * 12/2003  Garudadri ............... G10L 15/32
                                                      704/E15.049
7,778,831 B2 *  8/2010  Chen ....................... G10L 17/00
                                                      704/250
(Continued)

FOREIGN PATENT DOCUMENTS

CN    103236261 A    8/2013
CN    109147796 A    1/2019
(Continued)

OTHER PUBLICATIONS

International Search Report dated Jun. 2, 2021 issued by the International Searching Authority in International Application No. PCT/KR2021/001065 (PCT/ISA/210).
(Continued)

*Primary Examiner* — Edwin S Leland, III
(74) *Attorney, Agent, or Firm* — Sughrue Mion, PLLC

(57) ABSTRACT

An electronic apparatus is disclosed. The apparatus includes a memory configured to store at least one pre-registered voiceprint and a first voiceprint cluster including the at least one pre-registered voiceprint, and a processor configured to, based on a user recognition command being received, obtain information of time at which the user recognition command is received, change the at least one pre-registered voiceprint included in the first voiceprint cluster based on the obtained information of time, generate a second voiceprint cluster based on the at least one changed voiceprint, and based on a user's utterance being received, perform user recognition with respect to the received user's utterance based on the first voiceprint cluster and the second voiceprint cluster.

23 Claims, 29 Drawing Sheets

(51) Int. Cl.
*G10L 17/20* (2013.01)
*G10L 17/22* (2013.01)
*A61B 5/00* (2006.01)
G10L 25/66 (2013.01)
G10L 25/63 (2013.01)

(52) U.S. Cl.
CPC .............. *G10L 17/22* (2013.01); *G10L 25/63* (2013.01); *G10L 25/66* (2013.01)

(58) Field of Classification Search
USPC ........................................................ 704/246
See application file for complete search history.

(56) References Cited

U.S. PATENT DOCUMENTS

| | | | |
|---|---|---|---|
| 8,209,174 B2 * | 6/2012 | Al-Telmissani | G10L 17/06 704/238 |
| 8,571,867 B2 * | 10/2013 | Di Mambro | G07C 9/37 704/250 |
| 9,208,777 B2 * | 12/2015 | Yao | G10L 15/063 |
| 9,336,782 B1 * | 5/2016 | Patel | G10L 13/04 |
| 9,502,039 B2 * | 11/2016 | Foerster | G10L 25/84 |
| 9,792,894 B2 * | 10/2017 | Tachibana | G10L 13/04 |
| 9,804,822 B2 * | 10/2017 | Jung | G10L 17/20 |
| 9,865,266 B2 * | 1/2018 | Colibro | G10L 17/06 |
| 10,789,959 B2 * | 9/2020 | Kajarekar | G10L 17/04 |
| 10,911,600 B1 * | 2/2021 | Frenkel | G10L 17/08 |
| 2004/0246856 A1 * | 12/2004 | Fukushima | H04N 21/4415 386/E5.072 |
| 2007/0219801 A1 * | 9/2007 | Sundaram | G10L 17/04 704/270 |
| 2008/0122577 A1 * | 5/2008 | Gutta | G06F 21/32 340/5.52 |
| 2012/0249328 A1 * | 10/2012 | Xiong | G08B 21/22 340/541 |
| 2015/0078137 A1 * | 3/2015 | Lee | G07C 9/27 367/198 |
| 2016/0035350 A1 * | 2/2016 | Jung | G06F 3/167 704/275 |
| 2017/0365259 A1 * | 12/2017 | Zheng | G10L 17/02 |
| 2018/0144742 A1 * | 5/2018 | Ye | G10L 15/20 |
| 2018/0226079 A1 * | 8/2018 | Khoury | G10L 17/04 |
| 2018/0366128 A1 | 12/2018 | Liu et al. | |
| 2020/0005774 A1 * | 1/2020 | Yun | G10L 15/197 |
| 2020/0058293 A1 * | 2/2020 | Zhang | G10L 15/063 |
| 2020/0312337 A1 * | 10/2020 | Stafylakis | G10L 17/00 |
| 2021/0037136 A1 * | 2/2021 | Michaeli | G10L 17/02 |
| 2021/0256979 A1 * | 8/2021 | Zhang | H04R 1/08 |
| 2021/0375290 A1 * | 12/2021 | Hu | G10L 17/04 |
| 2021/0390959 A1 * | 12/2021 | Jain | G10L 17/20 |
| 2022/0301569 A1 * | 9/2022 | Khoury | G10L 15/26 |

FOREIGN PATENT DOCUMENTS

| | | | | |
|---|---|---|---|---|
| CN | 110400567 A | | 11/2019 | |
| EP | 3 790 006 A1 | | 3/2021 | |
| GB | 2556981 A | | 6/2018 | |
| JP | 2019101291 A | | 6/2019 | |
| JP | 7082444 B2 | | 6/2022 | |
| KR | 10-2016-0014297 A | | 2/2016 | |
| KR | 10-1981091 | * | 5/2019 | .......... H04N 21/488 |
| KR | 10-1981091 B1 | | 5/2019 | |
| KR | 1020200012963 A | | 2/2020 | |
| WO | 2008126254 A1 | | 10/2008 | |
| WO | WO-2018168369 A1 | * | 9/2018 | ............... A61B 5/00 |
| WO | 2020/000427 A1 | | 1/2020 | |

OTHER PUBLICATIONS

International Written Opinion dated Jun. 2, 2021 issued by the International Searching Authority in International Application No. PCT/KR2021/001065 (PCT/ISA/237).
Communication dated Dec. 28, 2021 issued by the Intellectual Property India in Indian Application English No. 202011024998.
Communication dated Jan. 5, 2023 issued by the European Patent Office in European Application No. 21824961.3.

* cited by examiner

FIG. 21

$$B_i = \min d(p, ci)_{cj}$$
$$B_1 = \min \{d(p1,c1)_{c2}, d(p1,c1)_{c3}\}$$
$$= d(p1,c1)_{c2}$$

2105

$$Qc_i = \frac{B_i - Aci}{\max\{B_i, Aci\}}$$

$$Qc_1 = \frac{d(p1,c1)_{c2} - Ac1}{\max\{d(p1,c1)_{c2}, Ac1\}}$$

$$= \frac{d(p1,c1)_{c2} - Ac1}{d(p1,c1)_{c2}}$$

2110

ELECTRONIC APPARATUS AND CONTROLLING METHOD THEREOF

CROSS-REFERENCE TO RELATED APPLICATION

This application is based on and claims priority under 35 U.S.C. § 119(a) of an India Patent Application No. 202011024998, filed on Jun. 15, 2020 in Intellectual Property India, and a Korean Patent Application No. 10-2020-0133183, filed on Oct. 15, 2020 in the Korean Intellectual Property Office (KIPO), the disclosures of which are incorporated by reference herein in their entireties.

BACKGROUND

1. Field

The present disclosure relates to an electronic apparatus and in particular, relates to an electronic apparatus that recognizes a user by analyzing the user's utterance.

2. Description of Related Art

Virtual personal assistance (VPA) based devices understand voice commands and thereby trigger occurrence of various tasks for a user, e.g. showing a map to a destination, rendering the latest news, switching on devices, rendering search results for a topic, etc. The devices may render final output acoustically or through a display or a combination of both.

In personalized VPA, the user can link and register his specific voice to an artificial intelligence (AI) driven acoustic device, a smart display, or a number of devices based on voice-based speaker recognition. Accordingly, via the personalized VPA, only a particular speaking human-being is authorized to switch ON/OFF or control a number of devices upon having been authenticated through speech, while denying access to others.

Contemporary personalized VPAs rely on stored and enrolled voice prints of one or more speakers registered with the device. As shown in FIG. 1, a speaker recognition system in the personalized VPAs operates by a two-step process. As a part of enrollment phase, a user is enrolled based on capturing voice from sample phrases uttered by the user. In recognition phase, an incoming utterance from the user spoken in real-time by the user is captured and compared with stored voiceprints based on the user trained model. Based on a similarity score, the speaking user is authenticated or rejected.

At least with respect to the personalized VPAs, the desired trait is context-driven personal assistance that delivers personalized answers to user's questions. The personalized responses from VPA to the user further augment secured access and maintain secrecy. However, human voice undergoes variation from time to time due to sickness, catching up with age, or any other external/internal reason. Accordingly, at least a user requirement associated with the personalized VPA is as follows:

How well the device understands the speaker's voice variability? and

How well the device overcomes the hurdle of voice variability and still authenticates the otherwise genuine user?

Voice variability refers to the variation in human voice due to health conditions (cold, alcohol intoxication, etc.), emotional state (e.g. stress, joy, etc.), aging, environmental noises, etc. Moreover, even for a particular condition, e.g. sickness, the human voice undergoes different degrees of variation for different persons. For example, a sick teenager's voice appears slightly varied during cold while the same may sound strikingly different during throat choke.

As has been duly observed, the speaker recognition system in the conventional VPAs and analogous devices substantially fails to take into account the speaker's voice variability during the authentication process and ends up rendering substantial false rejections. Referring to FIG. 1, for example, scenario 1, the user is suffering from cold. Under example scenario 2, the user is in an inebriated state. Both of such scenarios result in slight variation to voice. Other example scenarios may include old age, noisy background, emotional state, or any other compelling disability on part of the user. In an example, since the enrollment phase may have had the user's voice registered against a noisy background, even the background chaos could have been registered as a part of voiceprint. Meanwhile, the recognition phase receives the user's voice command against a clear background, thereby still leading to voice variability due to the absence of distortion.

Accordingly, the conventional speaker recognition mechanisms end up handing over false rejections to the user upon voice variations. Even if authentication somehow takes place, the same is achieved only upon receipt of a substantial number of repeated utterances from the user, thereby leaving the user frustrated at large. The situation further worsens in case the user is having a choked throat or has caught up with age.

At least a solution to prevent false rejections due to voice variations is to have a designated network entity to periodically collect voice data from user devices in a real environment, train/re-train (re-learn), and deploy a model at the user device. However, as the voice data carries sensitivity akin to any other confidential data, such collection of voice data amounts to an invasion of privacy. Even if privacy concerns were to be neglected, re-deployment of an updated model at the user device unnecessarily requires a re-enrolment of the already registered device for generating new voiceprints to accommodate the voice variability.

Accordingly, at least in view of the above description, the speech recognition based speaker authentication fairs low on a reliability quotient against other authentication systems, e.g. fingerprint-based system, retina based system, password/PIN-based system. Accordingly, there lies a need for a mechanism that can adapt itself automatically to overcome the challenge posed by voice variability during the enrolled speaker's authentication and prevents false rejections of the bonafide user.

Further, there lies a need for a mechanism to dynamically train the deployed speech recognition mechanism to overcome the above described challenges.

SUMMARY

This summary is provided to introduce a selection of concepts in a simplified format that are further described in the detailed description. This summary is not intended to identify key or essential inventive concepts of the disclosure, nor is it intended for determining the scope of the inventive concept.

According to an embodiment of the disclosure, an electronic apparatus includes a memory configured to at least one pre-registered voiceprint and a first voiceprint cluster including the at least one pre-registered voiceprint, and a processor configured to, based on a user recognition command being received, obtain information of time at which the user recognition command is received, change the at least one pre-registered voiceprint included in the first voiceprint cluster based on the obtained information of time, generate a second voiceprint cluster based on the at least one changed voiceprint, and based on a user's utterance being received, perform user recognition with respect to the received user's utterance based on the first voiceprint cluster and the second voiceprint cluster.

The processor may be configured to, based on the user recognition being successful, update the second voiceprint cluster based on the received user's utterance.

The processor may be configured to, based on the user recognition being successful, receive at least one of user activity information or user body information from an external device, and update the second voiceprint cluster based on the received at least one of user activity information or user body information.

The processor may be configured to validate an authority of the user based on failure of the user recognition, based on the user authority being validated, identify the user's health status based on the received user's utterance, and update the second voiceprint cluster based on the identified user's health status.

The processor may be configured to obtain voice feature from the received utterance, based on a mismatch between the obtained voice feature and the at least one pre-registered voiceprint and the at least one changed voiceprint, determine the user recognition as failure and validate an authority of the user, based on the user authority being validated, update the second voiceprint cluster based on the obtained voice feature, and perform user recognition based on the updated second voiceprint cluster.

The processor may be configured to identify a context corresponding to the obtained voice feature, identify a voice template corresponding to the identified context, based on a mismatch between the obtained voice feature and the at least one pre-registered voiceprint and the at least one changed voiceprint, validate the user authority based on the obtained voice feature and the identified voice template, and based on the user authority being validated, obtain cluster configuration information including a center value and a threshold value based on at least one of a voiceprint corresponding to the user among the obtained voice feature, the identified context, the identified voice template or the at least one pre-registered voiceprint, and update the second voiceprint based on the obtained cluster configuration information.

The processor may be configured to obtain a parameter other than the received utterance based on the mismatch between the obtained voice feature and the at least one pre-registered voiceprint and the at least one changed voiceprint, validate the user authority based on the obtained parameter, based on the user authority being validated, obtain cluster configuration information including a center value and a threshold value based on at least one of a voiceprint corresponding to the user among the obtained voice feature or the at least one pre-registered voiceprint, and update the second voiceprint cluster based on the obtained cluster configuration information.

The parameter may include at least one of an operation parameter corresponding to the user's operation performed on the electronic apparatus, an operation parameter corresponding to the user's operation performed on an external device, a biometric parameter corresponding to the user, or a time parameter for the user to access the electronic apparatus.

The processor may be configured to obtain an utterance voiceprint corresponding to the utterance based on the obtained voice feature, obtain a similarity value between the obtained utterance voiceprint, and the at least one pre-registered voiceprint and the at least one changed voiceprint, based on the obtained similarity value being smaller than a threshold value, determine failure of the user recognition, based on the obtained similarity value exceeding the threshold value, determine that the user recognition is successful, wherein the at least one pre-registered voiceprint is user identification information, wherein the at least one pre-registered voiceprint is included in the first voiceprint cluster, and wherein the first voiceprint cluster includes cluster configuration information including a predetermined center value and a predetermined threshold value.

The processor may be configured to, based on the mismatch between the obtained voice feature, and the at least one pre-registered voiceprint and the at least one changed voiceprint, validate the user authority based on sensing data obtained from a sensor or input data obtained through a user interface.

The memory may be configured to store at least one voice variability identifier (cluster ID) including at least one voice template, and the processor may be configured to obtain utterance voiceprint corresponding to the utterance based on the obtained voice feature, identify a voice variability identifier corresponding to the utterance voiceprint by comparing the obtained utterance voiceprint and the at least one voice template, and identify a context corresponding to the speech voiceprint based on the identified voice variability identifier, and the context may include at least one of intoxication, ill state, tired state, wake-up state, shout, murmur, whisper, agitated, throat-choked state, crooning, animated state, comical state.

The processor may be configured to obtain an embedding value by embedding the utterance voiceprint in a predetermined method, and based on a difference value between the obtained embedding value and a first center value of a first voiceprint cluster exceeding a first threshold value, and a difference value between the obtained embedding value and a second center value of a second voiceprint cluster exceeding a second threshold value, determine that user recognition is failed and validate a user authority.

The processor may be configured to, based on the user authority being validated, obtain a third center value and a third threshold value corresponding to the utterance voiceprint, obtain cluster configuration information including a fourth center value and a fourth threshold value based on the first center value, the first threshold value, the second center value, the second threshold value, the third center value, and the third threshold value, update the second voiceprint cluster based on the obtained cluster configuration information.

The processor may be configured to, based on a difference value between the obtained embedding value and the first center value of the first voiceprint cluster exceeding a fifth threshold value, and a difference value between the obtained embedding value and the second center value of the second voiceprint cluster exceeding the fifth threshold value, generate a third voiceprint cluster based on the acquired third center value and the third threshold value, and further register the generated third voiceprint cluster.

According to an embodiment of the disclosure, a control method of an electronic apparatus that stores a first voiceprint cluster including at least one pre-registered voiceprint, the method includes based on a user recognition command being received, obtaining information of time at which the user recognition command is received, changing the at least one pre-registered voiceprint included in the first voiceprint cluster based on the obtained information of time, generating a second voiceprint cluster based on the at least one of the changed voiceprint, and based on a user's utterance being received, performing user recognition with respect to the received user's utterance based on the first voiceprint cluster and the second voiceprint cluster.

The method may further include, based on the user recognition being successful, updating the second voiceprint cluster based on the received user's utterance.

The method may further include, based on the user recognition being successful, receiving at least one of user activity information or user body information from an external device; and updating the second voiceprint cluster based on the received at least one of user activity information or user body information.

The method may further include validating an authority of the user based on failure of the user recognition, based on the user authority being validated, identifying the user's health status based on the received user's utterance, and updating the second voiceprint cluster based on the identified user's health status.

The method may further include obtaining a voice feature from the received utterance, based on a mismatch between the obtained voice feature and the at least one pre-registered voiceprint and the at least one changed voiceprint, determining the user recognition as failure and validating an authority of the user, based on the user authority being validated, updating the second voiceprint cluster based on the obtained voice feature, and performing user recognition based on the updated second voiceprint cluster.

According to another embodiment of the disclosure, there is provided a computer program product comprising a non-transitory computer-readable recording medium having recording thereon a program for performing a control method of an electronic apparatus that stores a first voiceprint cluster including at least one pre-registered voiceprint in which the method includes, based on a user recognition command being received, obtaining information of time at which the user recognition command is received, changing the at least one pre-registered voiceprint included in the first voiceprint cluster based on the obtained information of time, generating a second voiceprint cluster based on the at least one changed voiceprint, and based on a user's utterance being received, performing user recognition with respect to the received user's utterance based on the first voiceprint cluster and the second voiceprint cluster.

To further clarify the advantages and features of the present inventive concept, a more particular description of the inventive concept will be rendered by reference to specific embodiments thereof, which is illustrated in the appended drawing. It is appreciated that these drawings depict only typical embodiments of the inventive concept and are therefore not to be considered limiting its scope. The inventive concept will be described and explained with additional specificity and detail with the accompanying drawings.

BRIEF DESCRIPTION OF THE DRAWINGS

These and other features, aspects, and advantages of the present inventive concept will become better understood when the following detailed description is read with reference to the accompanying drawings in which like characters represent like parts throughout the drawings, wherein:

FIGS. 11A and 1113 illustrate another example control-flow diagram depicting a sub-process in accordance with an embodiment of the present disclosure;

FIG. 21 is a view illustrating a calculation process used to obtain a quality parameter corresponding to a cluster.

Figure 1:
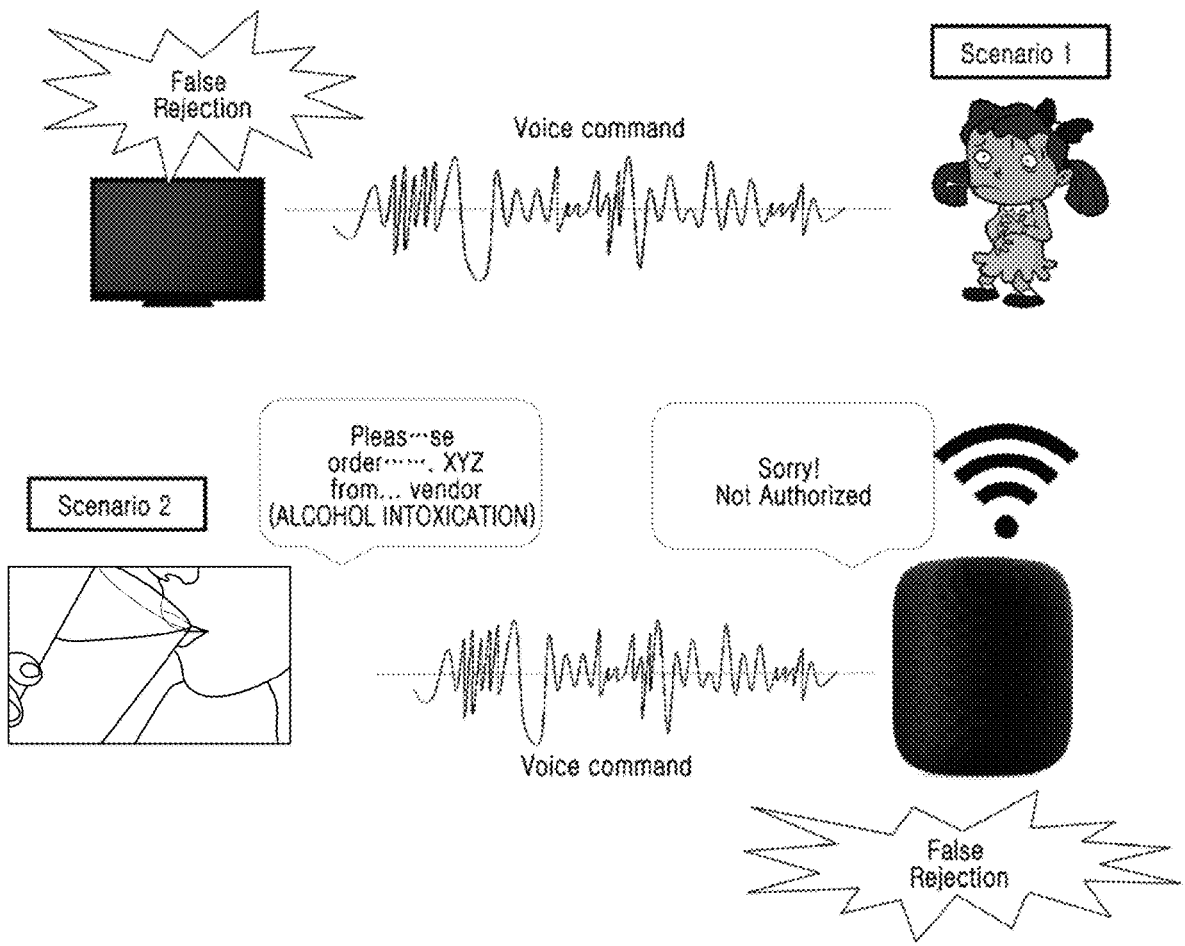
FIG. 1 illustrates examples of voice variability scenarios.

Further, skilled artisans will appreciate that elements in the drawings are illustrated for simplicity and may not have been necessarily been drawn to scale. For example, the flow charts illustrate the method in terms of the most prominent steps involved to help to improve understanding of aspects of the present inventive concept. Furthermore, in terms of the construction of the device, one or more components of the device may have been represented in the drawings by conventional symbols, and the drawings may show only those specific details that are pertinent to understanding the embodiments of the present inventive concept so as not to obscure the drawings with details that will be readily apparent to those of ordinary skill in the art having benefit of the description herein.

DETAILED DESCRIPTION

It should be understood at the outset that although illustrative implementations of the embodiments of the present disclosure are illustrated below, the present inventive concept may be implemented using any number of techniques, whether currently known or in existence. The present disclosure should in no way be limited to the illustrative implementations, drawings, and techniques illustrated below, including the exemplary design and implementation illustrated and described herein, but may be modified within the scope of the appended claims along with their full scope of equivalents.

The term "some" as used herein is defined as "none, or one, or more than one, or all." Accordingly, the terms "none," "one," "more than one," "more than one, but not all" or "all" would all fall under the definition of "some." The term "some embodiments" may refer to no embodiments or to one embodiment or to several embodiments or to all embodiments. Accordingly, the term "some embodiments" is defined as meaning "no embodiment, or one embodiment, or more than one embodiment, or all embodiments."

The terminology and structure employed herein is for describing, teaching and illuminating some embodiments and their specific features and elements and does not limit, restrict or reduce the spirit and scope of the claims or their equivalents.

More specifically, any terms used herein such as but not limited to "includes," "comprises," "has," "consists," and grammatical variants thereof do NOT specify an exact limitation or restriction and certainly do NOT exclude the possible addition of one or more features or elements, unless otherwise stated, and furthermore must NOT be taken to exclude the possible removal of one or more of the listed features and elements, unless otherwise stated with the limiting language "MUST comprise" or "NEEDS TO include."

Whether or not a certain feature or element was limited to being used only once, either way it may still be referred to as "one or more features" or "one or more elements" or "at least one feature" or "at least one element." Furthermore, the use of the terms "one or more" or "at least one" feature or element do NOT preclude there being none of that feature or element, unless otherwise specified by limiting language such as "there NEEDS to be one or more . . . " or "one or more element is REQUIRED."

Unless otherwise defined, all terms, and especially any technical and/or scientific terms, used herein may be taken to have the same meaning as commonly understood by one having an ordinary skill in the art.

Embodiments of the present inventive concept will be described below in detail with reference to the accompanying drawings.

FIG. 2 illustrates method-steps in accordance with an embodiment of the present disclosure.

Figure 2A:
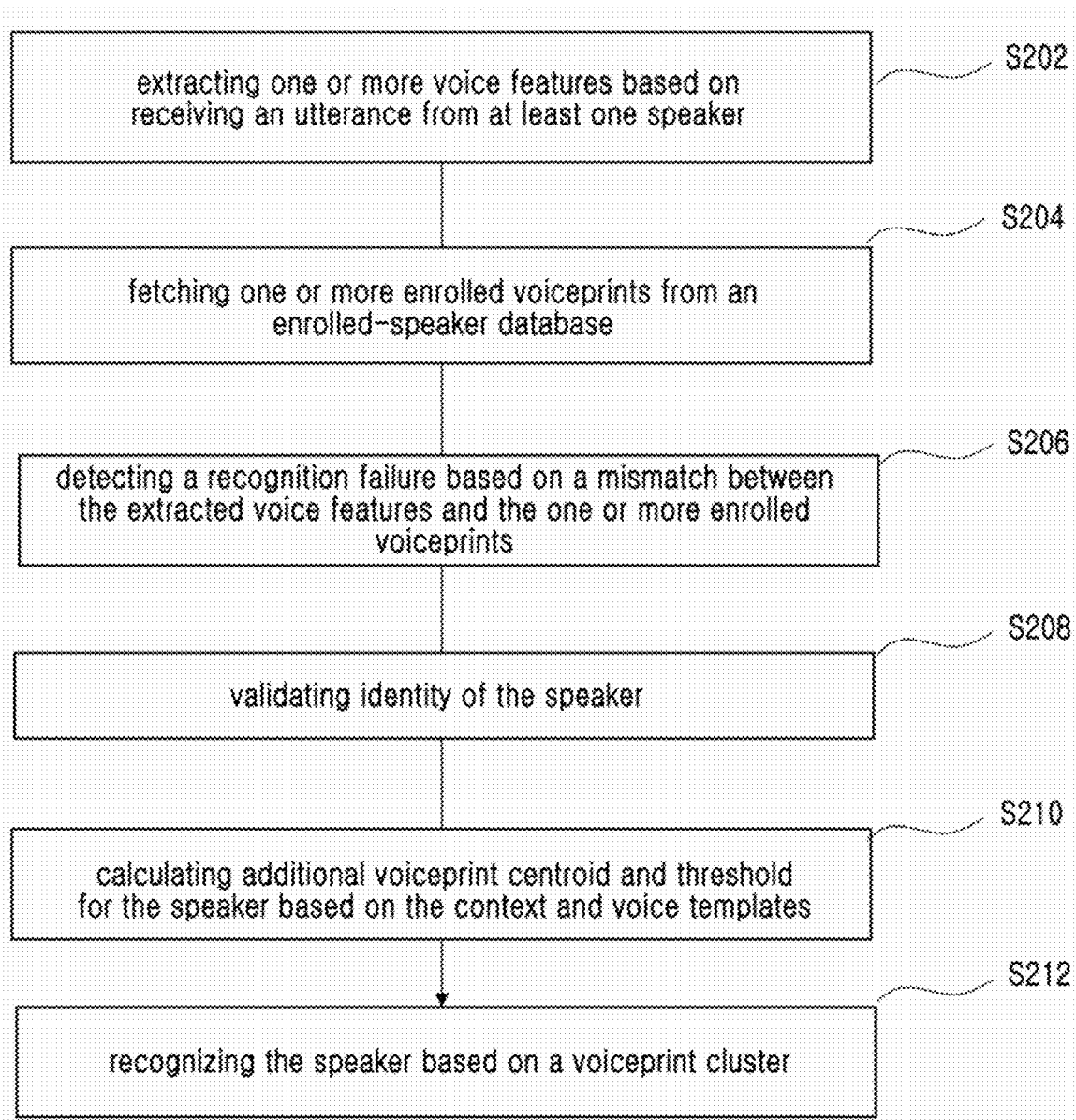
FIGS. 2A and 2B illustrate method steps in accordance with an embodiment of the present disclosure.

In an implementation as depicted in FIG. 2A, the present disclosure refers to a method for recognizing a speaker through a speech recognition based computing device. The method comprises extracting one or more voice features based on receiving an utterance from at least one speaker (S202). The extraction of the features comprises capturing the utterance through an acoustic sensor and resolving the captured utterance into one or more of pitch, tone, decibel, and frequency through speech processing criteria.

One or more enrolled voiceprints from an enrolled speaker database (i.e., speaker enrollment DB) are fetched (S204). Based the fetched voiceprints, a recognition failure is detected based on a mismatch between the extracted one or more voice-features and the one or more enrolled voiceprints (S206). The detection of the recognition-failure comprises computing a voice print based on the extracted voice features within the utterance. A similarity score of the computed voiceprint with respect to the enrolled voiceprint is calculated. The enrolled voiceprint is associated with a speaker identifier and defined by a cluster of voiceprints associated with a predetermined centroid (the centroid may refer to a mean value or a center value or a central value) and a threshold. Based thereupon, the recognition failure is detected based on the similarity score exceeding a threshold (S206).

The identity of the speaker is validated at least based on one or more of a) an alternate recognition method and b) one or more voice templates related to a context associated with the extracted voice features (S208). The determination of the context comprises computing a voiceprint related to the extracted voice-features in the utterance. One or more pre-defined voice templates are linked to at least one voice variability identifier (cluster ID) related to the computed voiceprint. The context determined based on the voice variability identifier is classifiable as a voice variability condition. In an example, the voice variability is defined by one or more of intoxication, ill-state, tired state, wake-up state, shout, murmur, whisper, agitated, throat-choked state, crooning, animated state, comical state.

In an embodiment, the identity of the speaker is validated based on the alternate recognition method (S208). The validation of the identity of the speaker based on the alternate recognition method involves one or more parameters other than the utterance extracted from non-acoustic sources. The validation is based on an implicit method defined by automatic sensing from sensors followed by a weighted average calculation, or by an explicit method defined by a received user input from a user.

The parameters other than the received utterance are defined by one or more operations performed over the speech recognition based computing device by the speaker, one or more operations performed by the speaker over one or more user equipment, at least one biometric-parameter pertaining to the speaker, and a temporal parameter associated with accessing of the speech recognition based computing device by the speaker. The recognition failure is determined as false by gathering the identity of the speaker based on an identification method involving one or more parameters other than the received utterance.

Additional voiceprint centroid and threshold are calculated (step 210) for the speaker based on the extracted one or more voice features and the one or more enrolled voiceprints to thereby generate a voiceprint cluster (S210). The computation of additional voice print centroid and threshold for the new voiceprint cluster comprises the calculation of a new centroid $C_i$ by shifting the predetermined voiceprint centroid to a location of computed voiceprint and by executing at least one of: a) changing the predetermined threshold, and b) maintaining the predetermined threshold.

The recognition of the speaker is enabled based on the new calculated centroid $C_i$ as an unknown variability cluster (S212). A storage operation is performed in the enrolled user database by storing the unknown variability cluster as the enrolled voiceprint. In other examples, the delta centroid value and the delta threshold value corresponding to the unknown variability cluster are calculated and stored as representing the variability cluster. Accordingly, the enrolled speaker database is updated with a voiceprint cluster comprising the calculated values for enabling recognition.

Figure 2B:
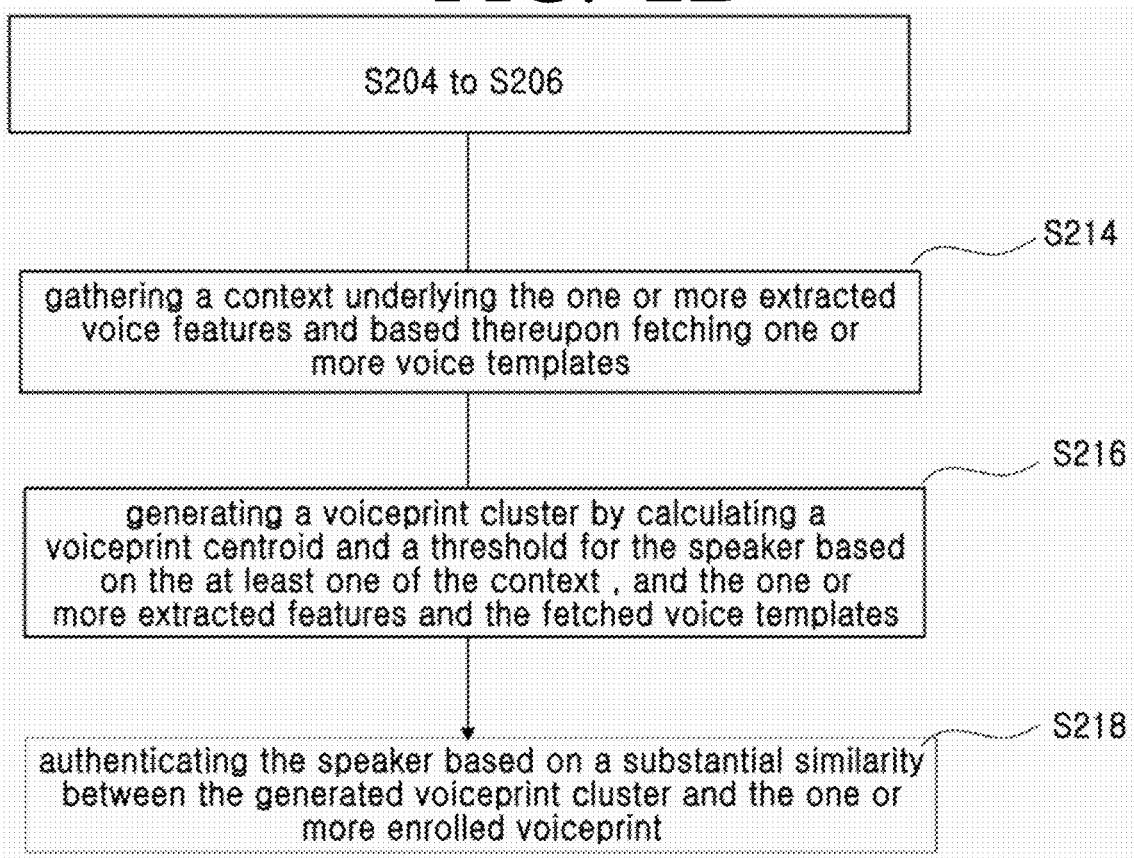

In other embodiments as depicted in FIG. 2B, the steps 202 to 206 form the precursor and are similar to FIG. 2A. Thereafter, a context underlying the one or more extracted voice features are gathered, and based thereupon one or more voice templates are fetched (S214). In other words, the validating of the identity in FIG. 2B is based on one or more voice templates and the context associated with the one or more extracted voice features. In other examples, the determination of the context comprises determining the separation of the computed voiceprint from one or more of a) enrolled voiceprint and b) one or more variability cluster with respect to the enrolled speaker. The context is determined as unknown voice variability based on detecting the separation as exceeding the pre-determined threshold.

A voiceprint cluster is generated by calculating a centroid and a threshold for the speaker based on the at least one of the context, and the one or more extracted features and the fetched voice templates (S216). The identity of the speaker is validated or the speaker is authenticated based on a substantial similarity between the generated voiceprint cluster and the one or more enrolled voiceprints, thereby authenticating the speaker (S218).

Further, the voiceprint cluster generation in step 216 corresponds to the calculation of additional voiceprint centroid and threshold for the speaker based on the at least one of the context, fetched voice template and the at least one enrolled voiceprint. Such computation for the new voiceprint cluster comprises the calculation of a new centroid $C_i$ and a new threshold value $T_i$ from a) the predetermined voiceprint centroid and threshold; and b) a delta centroid and a delta threshold value associated with the voice variability identifier linked with the determined context. Based on the new centroid $C_i$ and the new threshold value $T_i$ as a variability cluster of the at least one speaker in the enrolled speaker database, the recognition of the speaker is achieved.

Figure 3:
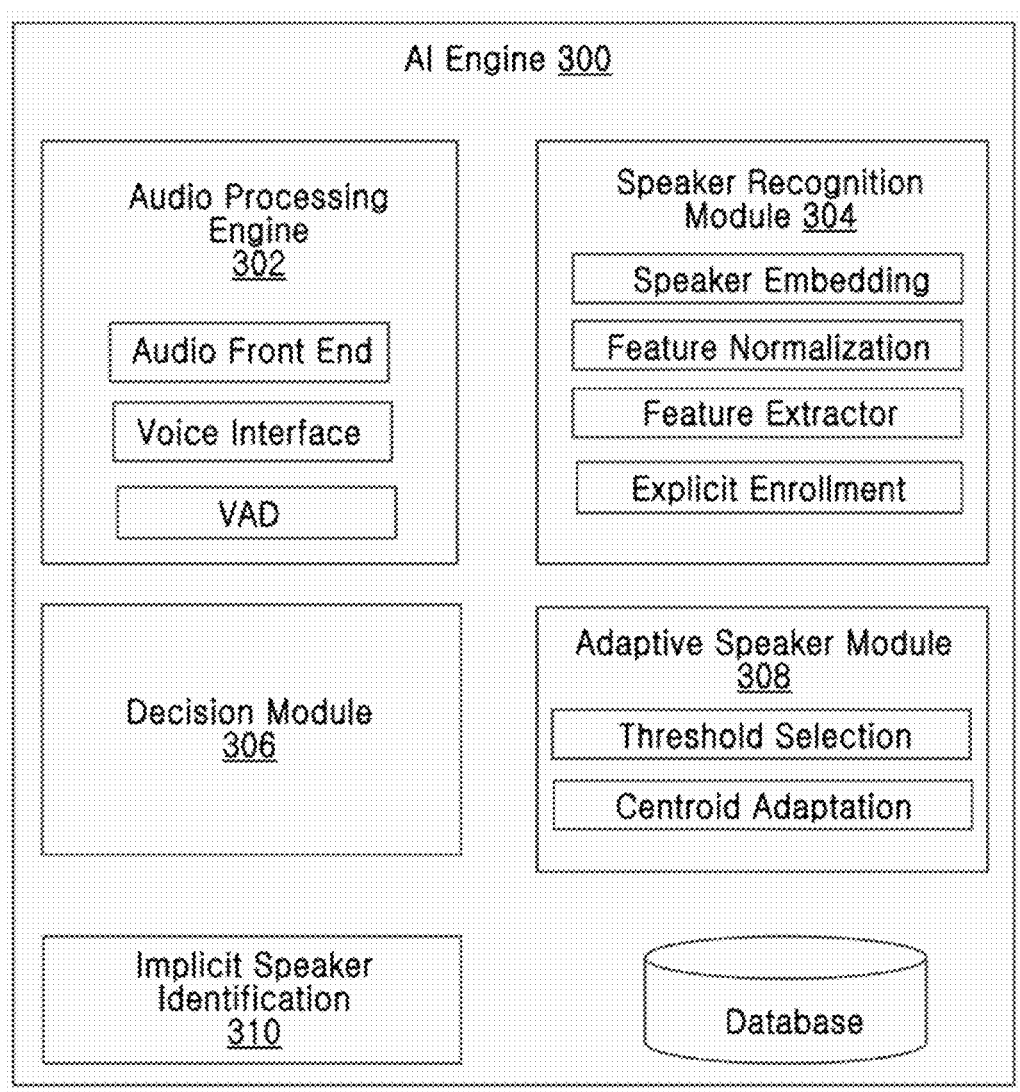
FIG. 3 illustrates an implementation of the method steps of FIGS. 2A and 2B, in accordance with an embodiment of the present disclosure.

FIG. 3 illustrates an overview of detailed computing architecture facilitated by the acoustic and non-acoustic sensor and automatic speech recognition (ASR) modules for implementing the method steps of FIGS. 2A and 2B. The architecture represents a system 300 for recognizing a speaker in a speech recognition based computing device may be referred to as an artificial intelligence (AI) powered system. The system 300 may be interchangeably referred to as an AI engine 300.

The system 300 comprises an audio processing engine 302 executing the step 202 and processing the user's input raw voice for thereby extracting a clean signal. A speaker recognition module 304 (or recognition model) executes the steps 202 and 204 for processing the clean voice sample, extracting the voice features, and generating the speaker embedding for a decision module 306.

In an implementation, the speaker recognition module 304 converts the speech into a computer-readable text using an automatic speech recognition (ASR) model. The user's intent of utterance may be obtained by interpreting the converted text using a natural language understanding (NLU) model. The ASR model or NLU model may be an artificial intelligence model. The artificial intelligence model may be processed by an artificial intelligence dedicated processor designed in a hardware structure specified for artificial intelligence model processing. The artificial intelligence model may be obtained by training. In addition, the speaker recognition module 304 converts the speech into a computer-readable text using 'Speaker Embedding', 'Feature Normalization', 'Feature Extractor' and 'Explicit Enrollment'.

Here, "obtained by training" means that a predefined operation rule or artificial intelligence model configured to perform the desired feature (or purpose) is obtained by training a basic artificial intelligence model with multiple pieces of training data by a training technique. The artificial intelligence model may include a plurality of neural network layers. Each of the plurality of neural network layers includes a plurality of weight values and performs neural network computation by computation between a result of computation by a previous layer and the plurality of weight values. Language understanding is a technique for recognizing and applying/processing human language/text and includes, e.g., natural language processing, machine translation, dialog system, question answering, or speech recognition/synthesis.

The decision module 306 executes the step 206 and processes the speaker embedding mapped with enrolled sample embedding using similarity criteria, and produces the results. If the user is not identified at this point, it detects voice variability conditions and adjusts the threshold value accordingly to handle known voice variability and prevents false rejections.

An adaptive speaker module 308 executes the steps 208, 210, and 212. The adaptive speaker module 308 processes currently captured or test voice samples received from the decision module and updates a threshold based on implicit authentication methods in case of failure of the speech based speaker recognition method at authentication. It also updates the centroid of a voiceprint cluster to enhance system performance.

Based on a received voice sample based on which the user has been authenticated despite voice variability, the decision module 306 decides if the voice sample needs to be further processed by the adaptive speaker module 308 (or speaker model) for conversion into a voiceprint through a local model update. In another scenario, the decision module 306 decides if the stored voice features in the database (DB) need to be shared with a remote central server for requesting global model update as referred in FIG. 9.

An implicit speaker identification module 310 authenticates the speaker based on readings obtained from external elements such as sensors and thereby assists the decision module 306 in detecting false rejections.

Figure 4A:
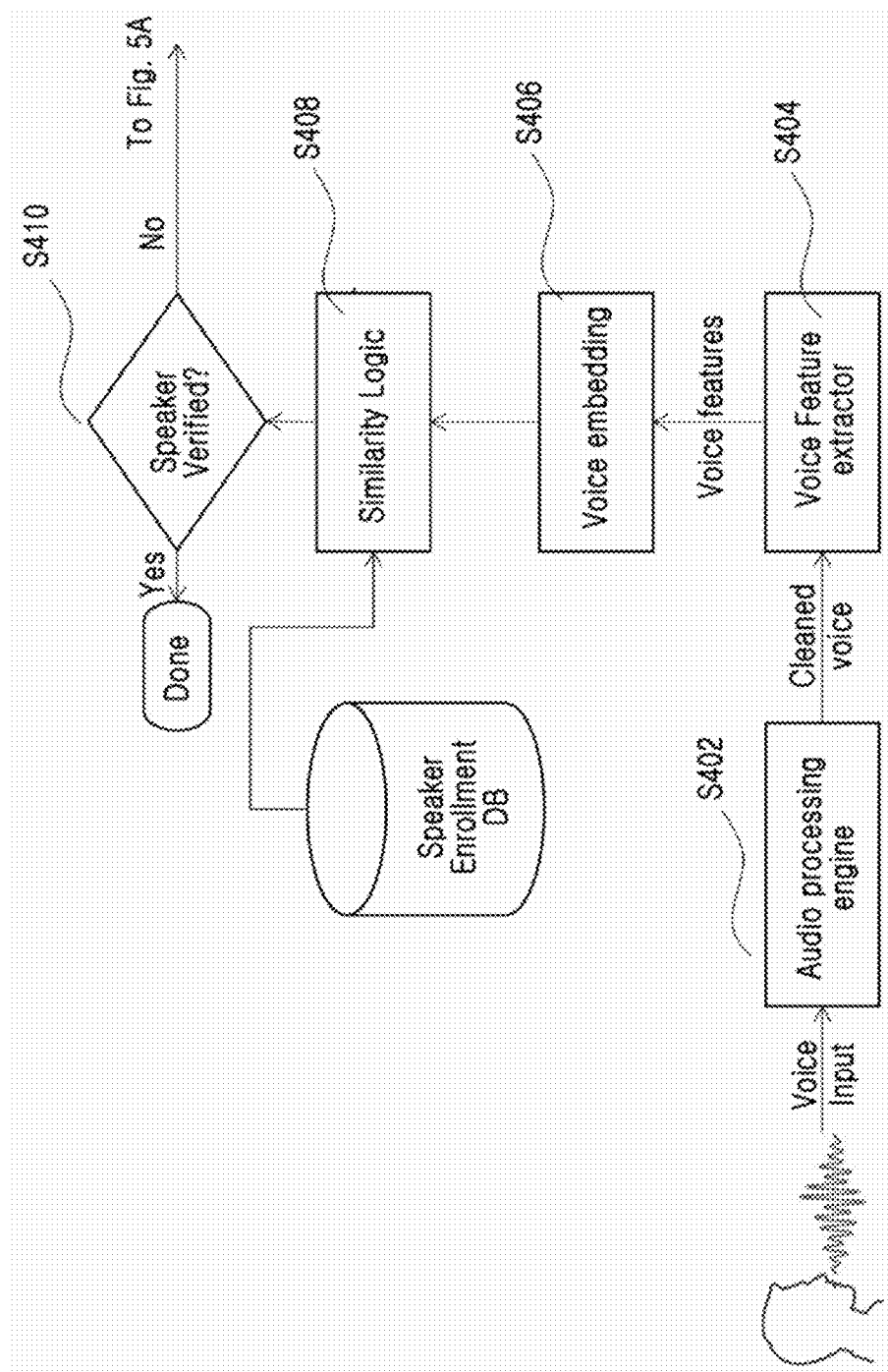
FIGS. 4A, 4B and 4C illustrate an example control flow diagram depicting a sub-process in accordance with an embodiment of the present disclosure.

FIG. 4A illustrates speaker verification procedure in accordance with an embodiment of the present disclosure and accordingly at least refers to the steps 202 to 206 of FIG. 2A.

Step 402 corresponds to an operation of audio processing engine 302 and refers to capturing an utterance from the speaker through an acoustic sensor. A VAD (voice activity detection) module detects the presence of human voice. Thereafter, upon detection of human voice, the VAD module triggers operation of the speech processing criteria for rendering a clean voice output. The acoustic sensor, VAD and the speech processing criteria collectively denote the front-end electronics of the audio processing engine.

Step 404 relates to extraction of one or more voice features based on received clean voice through the step 402 from the audio processing engine 302. The extracted voice features comprise pitch, tone, decibel, and frequency. The features may be extracted as a part of operation of an artificial neural network (ANN).

Step 406 refers to generation of voice embedding to be used as a biometric for authenticating the speaker. The embedding may be generated as a part of operation of the artificial neural network (ANN). The ANN may be configured to transform a speaker voice to an embedding space or latent space, where similar voices are clustered near each other and different voices are far away from each other.

Overall, the steps 404 to 406 depict the operation of the audio processing engine 302 (or processing module) and the speech recognition module 304 in FIG. 3 and accordingly collectively refer to step 202 of FIG. 2.

Figure 4B:
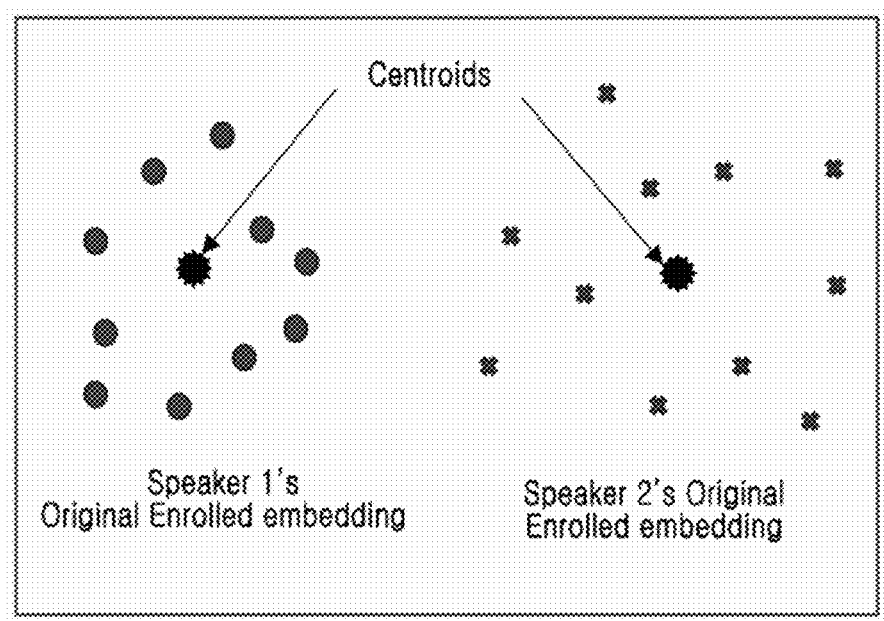

Step 408 refers to step 204 and illustrates a comparison of the currently received voice features (i.e., voice embedding as generated in the step 406) with the enrolled voiceprints obtained by the speech recognition module 304 based on a similarity criterion. By default for each speaker, an arithmetic mean position (based on cosine distances) of enrolled voiceprints is calculated as centroid voiceprint, which is voiceprint cluster centered on the centroid and defined by a threshold. The centroid approach minimizes the effect of variations within the enrollment data while maintaining the general spatial location of the speaker's cluster. In an example, FIG. 4B depicts the enrolled voiceprint clusters for the two users, Speaker 1 and Speaker 2 which are stored in a speaker enrollment DB.

Figure 4C:
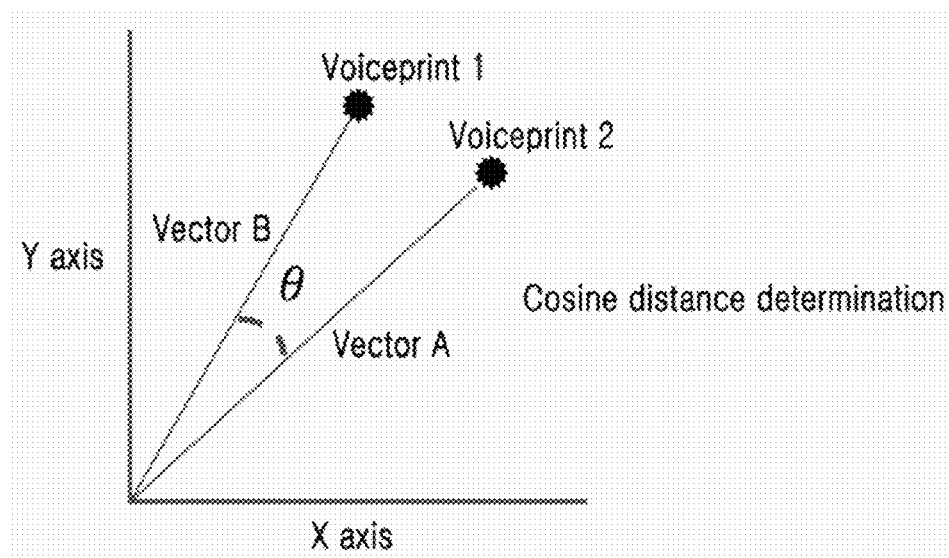

As a part of speaker verification during the step 408 and as depicted in FIG. 4C, a cosine distance is calculated between the centroid and the test voiceprints corresponding to the captured voice features and this distance is compared with a threshold value to deem an identified speaker. Given two vectors of attributes, A and B, the cosine similarity, is represented using a dot product of magnitudes as:

$$\text{Cosine Similarity} = \frac{A \cdot B}{\|A\| \cdot \|B\|} = \frac{\sum_{i=1}^{N} A_i B_i}{\sqrt{\sum_{i=1}^{N} A_i^2} \sqrt{\sum_{i=1}^{N} B_i^2}}$$

Cosine distance = 1 − Cosine Similarity

As a part of threshold selection, for each speaker's enrolled voiceprint i, the cosine distance di from the centroid is calculated. Variance and standard deviation is calculated assuming voiceprints are in half normal distribution as:

$$\text{mean distance } (d') = \frac{\sum_{i=1}^{N} d_i}{N}$$

$$\text{vairance } (V) = \left(\frac{\sum_{i=1}^{N} (d_i - d')^2}{N}\right)\left(1 - \frac{2}{\pi}\right)$$

$$\text{std. deviation } (D) = \sqrt{V} = \sqrt{\left(\frac{\sum_{i=1}^{N} (d_i - d')^2}{N}\right)\left(1 - \frac{2}{\pi}\right)}$$

Here, the threshold is selected as 3×std. deviation to cover 99.7% of point.

At the step 408, a test voiceprint is generated for the input voice and a similarity score is calculated based on comparison with the original centroid C and the threshold (shown in FIG. 4B and FIG. 5B) associated with enrolled voiceprints of each registered user. If the cosine similarity is detected, then the user is said to have been authenticated at step 410.

At the step 410, which refers to the step 206, the voice recognition failure is detected in case of similarity logic finding the voice features or the test voiceprint. Accordingly, the control transfers to step 502 of FIG. 5A.

Figure 5A:
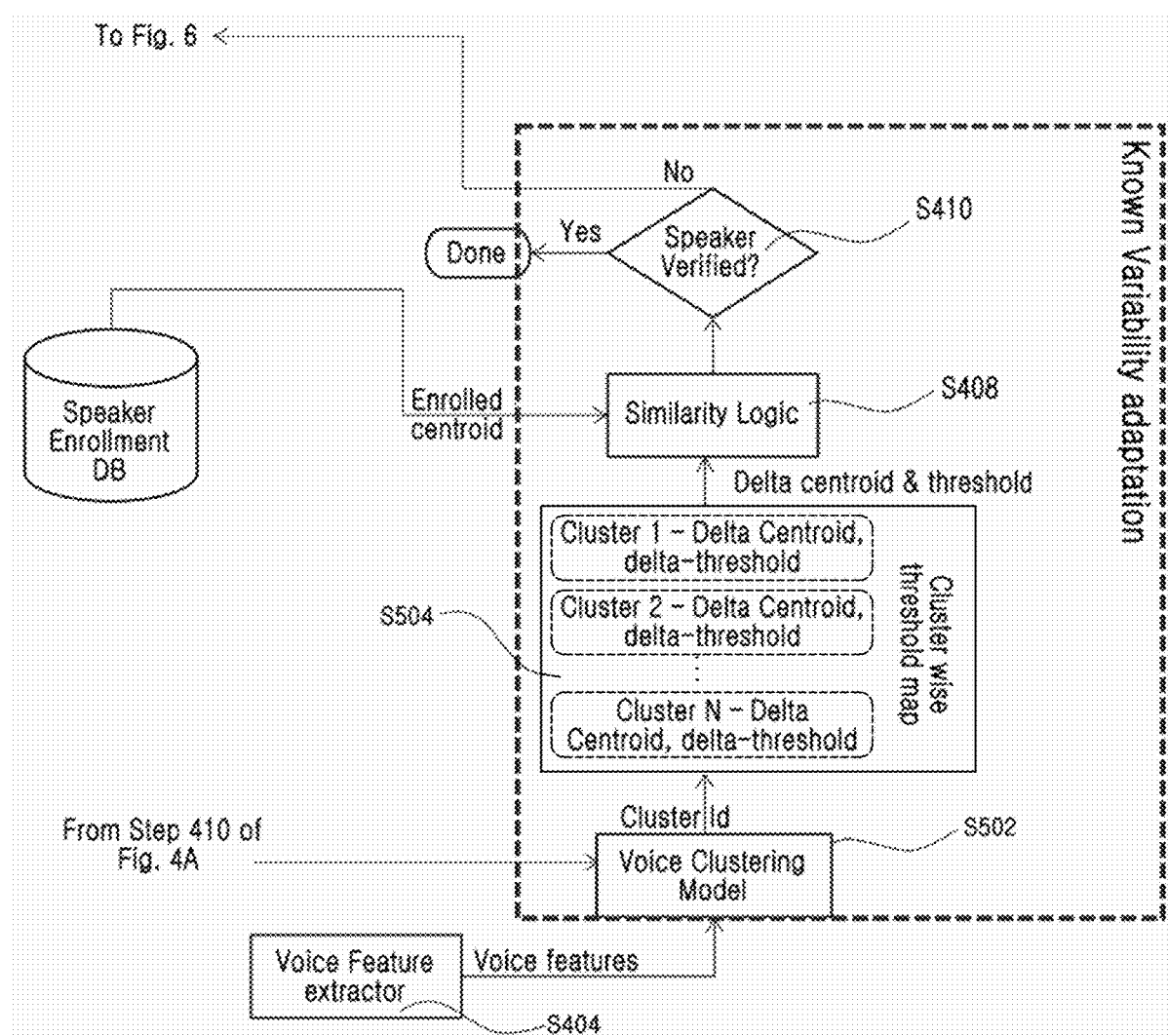
FIGS. 5A and 5B illustrate another example control-flow diagram depicting a sub-process in accordance with an embodiment of the present disclosure.
Figure 5B:
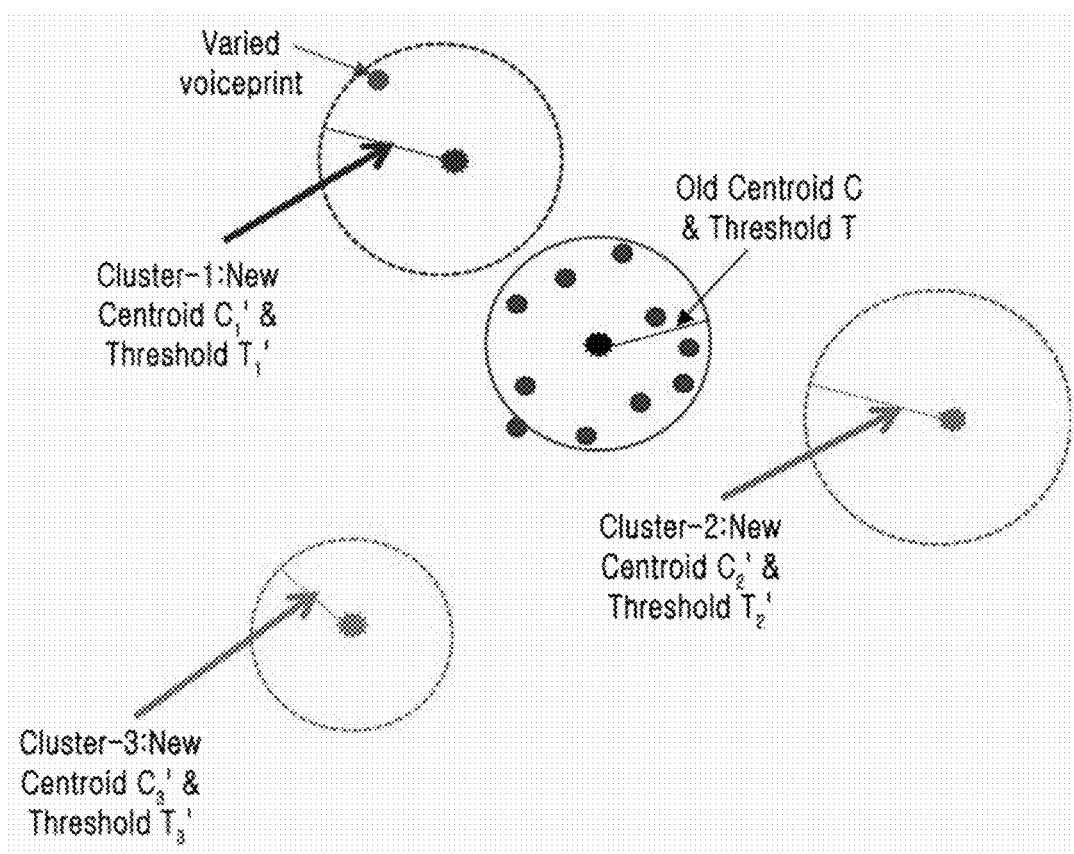

FIGS. 5A and 5B illustrate variability detection and adaptation and accordingly refer the operational interaction of the decision module 306 and the adaptive speaker module 308 for executing steps 214 to 218 of FIG. 2B.

Example common causes behind voice variability are the common cold, alcohol intoxication, changes due to time of the day (e.g., voice changes after waking-up in the morning, etc.). These variations may cause the system 300 to fail and render false rejections for the otherwise bonafide user. However, the system 300 handles these hurdles posed by common voice variations to prevent falsely rejecting speaker voice identification.

In operation, a clustering module is trained (e.g., at server side) based on standard human voice features as input and assists the creation of a cluster for each variation. In an example and as depicted in FIG. 5B, Cluster-1 denotes voice variability due to "cold", Cluster-2 denotes alcohol intoxication, Cluster-3 denotes morning voice, etc.

In an example for each of these variations i, a threshold delta value ∂t i and a centroid delta vector ∂ci are determined based on as follows:

| Delta threshold (∂t) | Delta centroid vector (∂c) |
|---|---|
| ∂t1 - Delta threshold (%) value for variation cluster 1 (e.g. Cold) | ∂c1 - Delta centroid vector of size (N × 1) for variation cluster 1 (Cold) |
| ∂t2 - Delta threshold (%) value for variation cluster 2 (e.g. Alcohol intoxication) | ∂c2 - Delta centroid vector of size (N × 1) for variation cluster 2 (Alcohol intoxication) |
| ∂t3 - Delta threshold (%) value for variation cluster 3 (e.g. Morning voice) | ∂c3 - Delta centroid vector of size (N × 1) for variation cluster 3 (Morning voice) |
| ∂t4 - Delta threshold (%) value for variation cluster 4 (e.g. Emotional-Happy) | ∂c4 - Delta centroid vector of size (N × 1) for variation cluster 4 (Emotional-Happy) and so on. |

Here, (N×1) is the size of voiceprint vector output by the speaker recognition model. A cluster delta map [Cluster-id, (∂t, ∂c)] is created based on these values and deployed on a user device as part of a voice recognition package. Such a map allows accessing ∂t, ∂c based upon a cluster id.

In operation of FIG. 5A, at step 502, based on the current voice features from the step 404 and the voice recognition trigger received from step 408 of FIG. 4A, the clustering module selects a variation cluster-id. In an example, the module accepts voice features and optionally external data (e.g., current time of the day and health data from a wearable device if available) as input and predicts the corresponding variation cluster ID.

Based on this predicted cluster-id i, delta threshold ∂ti and delta centroid ∂ci are retrieved from cluster threshold map. These deltas are then used to calculate a new centroid Ci and a new threshold value Ti is calculated as follows:

Centroid $C_i = C + \partial ci$

A. $\begin{bmatrix} v'_0 \\ v'_1 \\ v'_2 \\ \vdots \\ v'_N \end{bmatrix} = \begin{bmatrix} v_0 \\ v_1 \\ v_2 \\ \vdots \\ v_N \end{bmatrix} + \begin{bmatrix} \partial v_0 \\ \partial v_1 \\ \partial v_2 \\ \vdots \\ \partial v_N \end{bmatrix} = \begin{bmatrix} v_0 + \partial v_0 \\ v_1 + \partial v_1 \\ v_2 + \partial v_2 \\ \vdots \\ v_N + \partial v_N \end{bmatrix}$ ii. & Threshold $T_i = T \times \left(1 + \frac{\partial ti}{100}\right)$ At step 504, on applying delta threshold ∂ti and delta centroid ∂ci for variability i, to speaker's personalized threshold T and centroid C, respectively (see, equation above), new personalized threshold Ti and centroid Ci for variability i for that speaker is resulted as Cluster 1, Cluster 2 and Cluster 3 as shown in FIG. 5B.

Thereafter, the new personalized threshold Ti and centroid Ci for variability i undergo the step 408 of FIG. 4A, via the similarity logic to determine the speaker Id or the speaker identifier of the input voice and, based thereupon, authenticate the speaker via step 410. If the user is still not authenticated, then the control transfers to FIG. 6.

Figure 6:
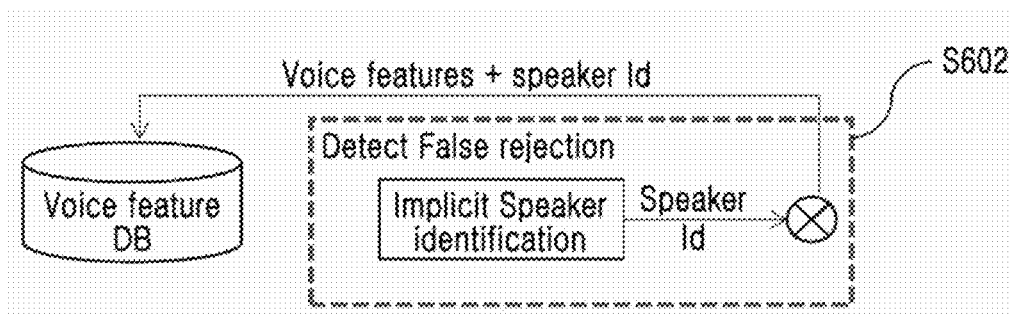
FIG. 6 illustrates another example control-flow diagram depicting a sub-process in accordance with an embodiment of the present disclosure.

FIG. 6 illustrates step 602 detecting false rejection based on authentication through an alternate recognition method and accordingly corresponds to the step 208 of FIG. 2A and the operation of the implicit speaker identification module 310 of FIG. 3. When the system 300 (or AI engine) is unable to identify the registered speaker's voice for otherwise genuine registered speaker, it is called false rejection. The step 602 detects false rejection through the alternate recognition method and accordingly predicts the speaker Id for utterance implicitly or automatically without user intervention using various sensors/methods In an example, as a part of the step 602, following modalities/features may be observed by the device to identify the speaker:

x1—Use of personalized wakeup words;

x2—First few actions done on the device (e.g. First application opened, specific content (text, image, video accessed));

x3—Personalized Device control (e.g. Device handling, remote handling);

x4—Speaker-device co-relation (Relation between user accompanied devices) near the target device where a user is speaking;

x5—Other biometrics (if available without user intervention such as face recognition, touch sensor); and x6—Time context of accessing the device.

A confidence score can be evaluated based on available features at the time of the speaker speaking to the device as follows:

Confidence $C = f(x_1, x_2, x_3, x_4, x_5, x_6)$

A. $= x_1 \cdot w_1 + x_2 \cdot w_2 + x_3 \cdot w_3 + x_4 \cdot w_4 + x_5 \cdot w_5 + x_6 \cdot w_6$ The weights (w1, w2, . . . , wn) may be learnt statistically, for example, by a frequentist method or by machine learning (ML) enabled probabilistic learning.

As a part of statistical frequentist method, if Number of occurrences of implicit feature x is Nx and Number of occurrences when a user was recognized through voice or other explicit features is Ne, then weight wx corresponding to an implicit feature x is given by:

$$w_x = \frac{N_x}{N_e}$$

wx ranges from 0 to 1, representing the reliability of feature x in predicting speaker's presence. So, if wx=1, feature x can predict the speaker's presence most reliably.

Figure 22:
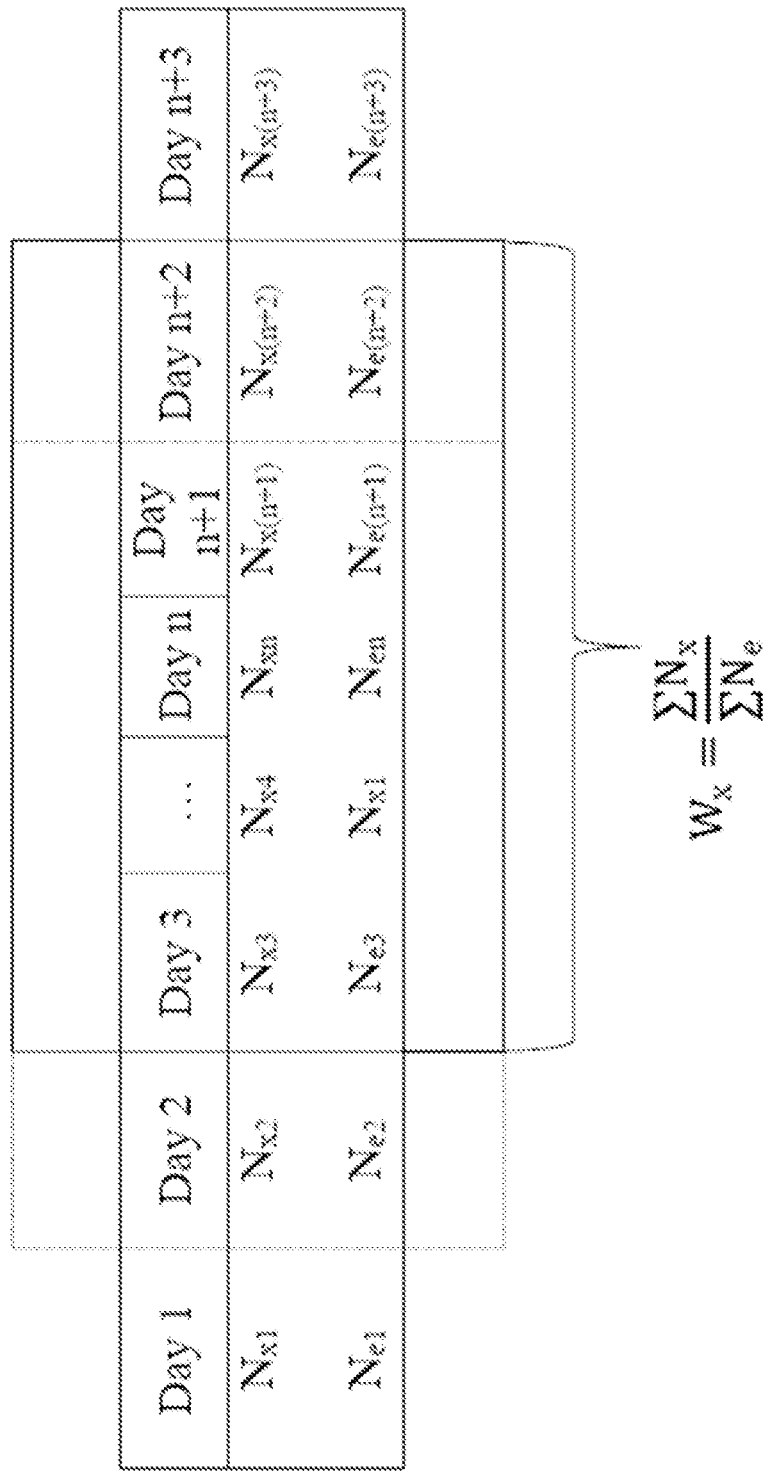
FIG. 22 illustrates an example of a sliding window method for calculating a weight in accordance with an embodiment of the disclosure.

The weight wx is calculated based on historic device usage data collected within a predefined time period (e.g., 'n' days). As it may change based on changes in device usage behavior, weight calculation may be done in a sliding window method. In an example, the sliding window example is represented in FIG. 22.

In other-example, as per learning method, weights can be learnt through a logistic regression method.

Accordingly, upon the derivation of the speaker id through adoption of any of the above described methods as the alternate recognition method, the user is identified and speech based speaker recognition that rejected the speaker in FIG. 5A is deemed as false rejections. Thereafter, the control transfers to FIG. 7.

Figure 7:
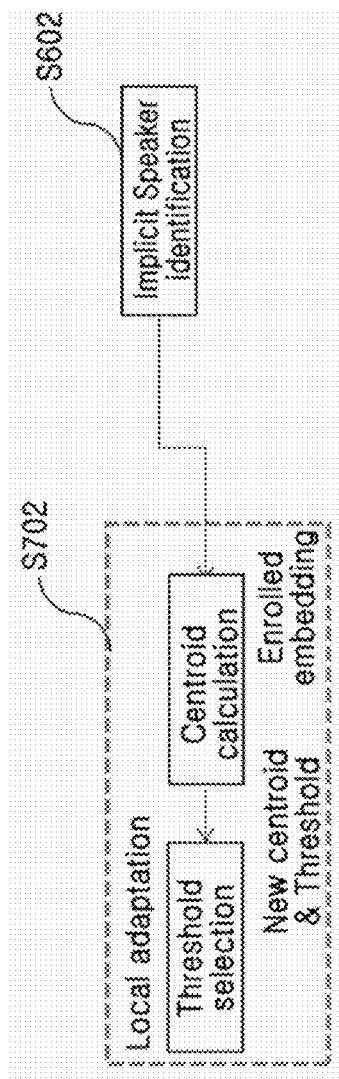
FIG. 7 illustrates another example control-flow diagram depicting a sub-process in accordance with an embodiment of the present disclosure.

FIG. 7 illustrates local adaptation based method (S702) and accordingly refers to the operation of the adaptive speaker module 308 and the step 210 of FIG. 2.

During verification, it is ascertained that the test voiceprint or new voiceprint (corresponding to the present voice features) lies beyond the threshold boundaries of the enrolled voiceprint cluster (as depicted in FIG. 4B) as well as known variability clusters (as depicted in FIG. 5B). However, since the false rejection has been determined and detected at step 602, such a new voiceprint is nonetheless trustworthy and included in the speaker enrollment DB and treated as part of a new unknown variability cluster proposed to be calculated for the speaker.

As a part of such calculation, the threshold value is kept constant (i.e., $\partial t_{new}=0$), and the original centroid is shifted to include the newly added voiceprint.

When false rejection is detected, it means that the new voiceprint lies at a distance greater than the threshold from the centroid.

Figure 8A:
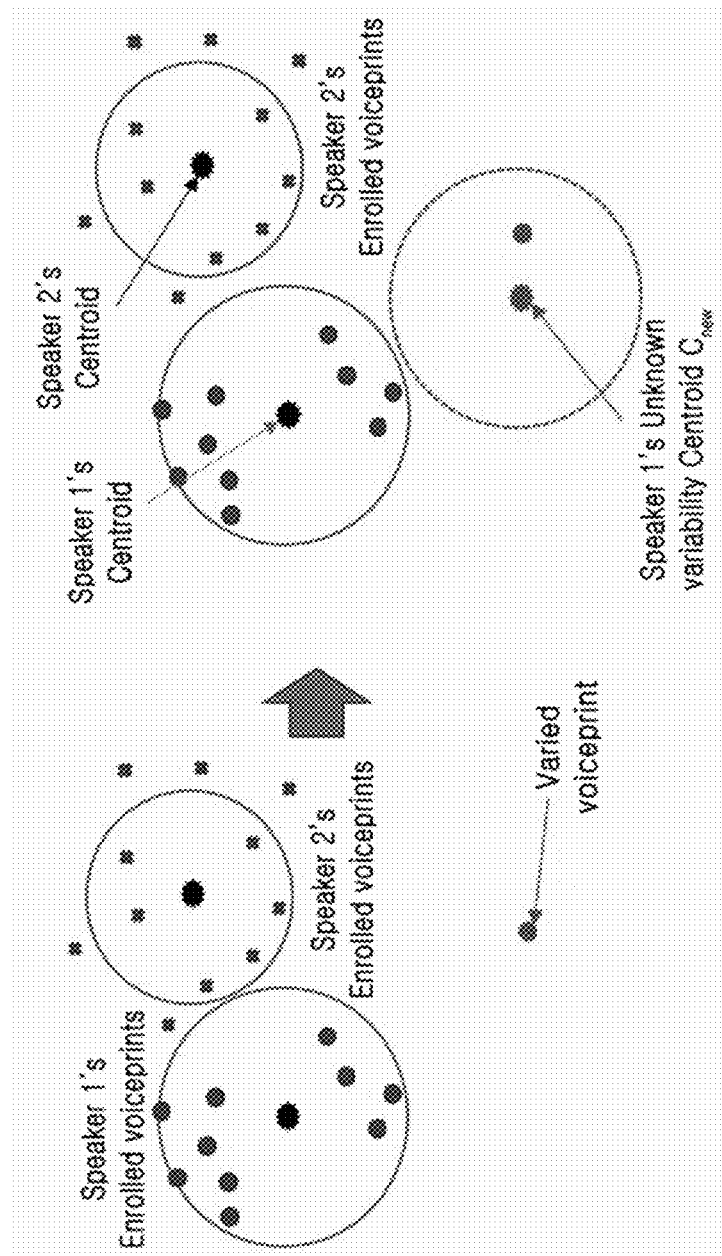
FIGS. 8A and 8B illustrate an example implementation of the sub-process of FIG. 7, in accordance with an embodiment of the disclosure.
Figure 8B:
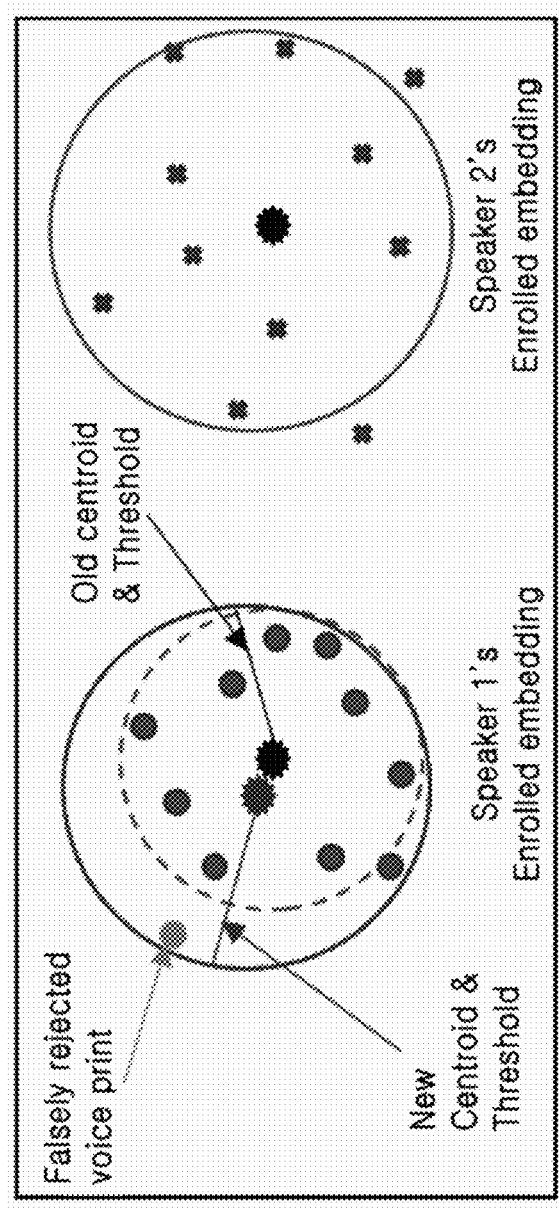

FIGS. 8A and 8B illustrate an example implementation of the sub-process of FIG. 7, in accordance with an embodiment of the disclosure. In an example as referred in FIG. 8A, false rejection occurs for speaker 1 and the test voiceprint or the varied voiceprint is observed as substantially away from the as enrolled voiceprints. In this case, the user is identified as speaker 1 as detected by the implicit speaker identification module 310. As the new voiceprint is located beyond the threshold distance from the centroid, recalculation of the threshold and the centroid is required in order to include this voiceprint within identifiable range.

Accordingly, a voiceprint cluster is generated in FIG. 8A as corresponding to the unknown variability which is centered upon the centroid Cnew. Such cluster accommodates the varied voiceprint. FIG. 8B illustrates as to how new-centroid is calculated for the unknown variability of speaker 1. Such calculation involves either slightly shifting of the centroid in new voiceprint's direction or, the threshold slightly increased or, both. As specifically referred in FIG. 8B, the new voiceprints (corresponding to false rejection occurring for speaker 1) are included as enrolled voiceprint and such new voiceprint is beyond the threshold distance and still eligible for enrollment. This inclusion results in increasing in the threshold distance as well as a slight shifting in centroid position. In other examples, the shifting of the centroid done to accommodate the test voiceprint does not involve a change in threshold value.

In an example, for this new variability based voiceprint cluster, fresh delta values are created as corresponding to the voice variability specific to the newly created voiceprints. Such delta values may be calculated as:

Delta–threshold $\partial t\text{new}=0$ &

Delta–Centroid $\partial C\text{new}=C'-C$

Figure 9:
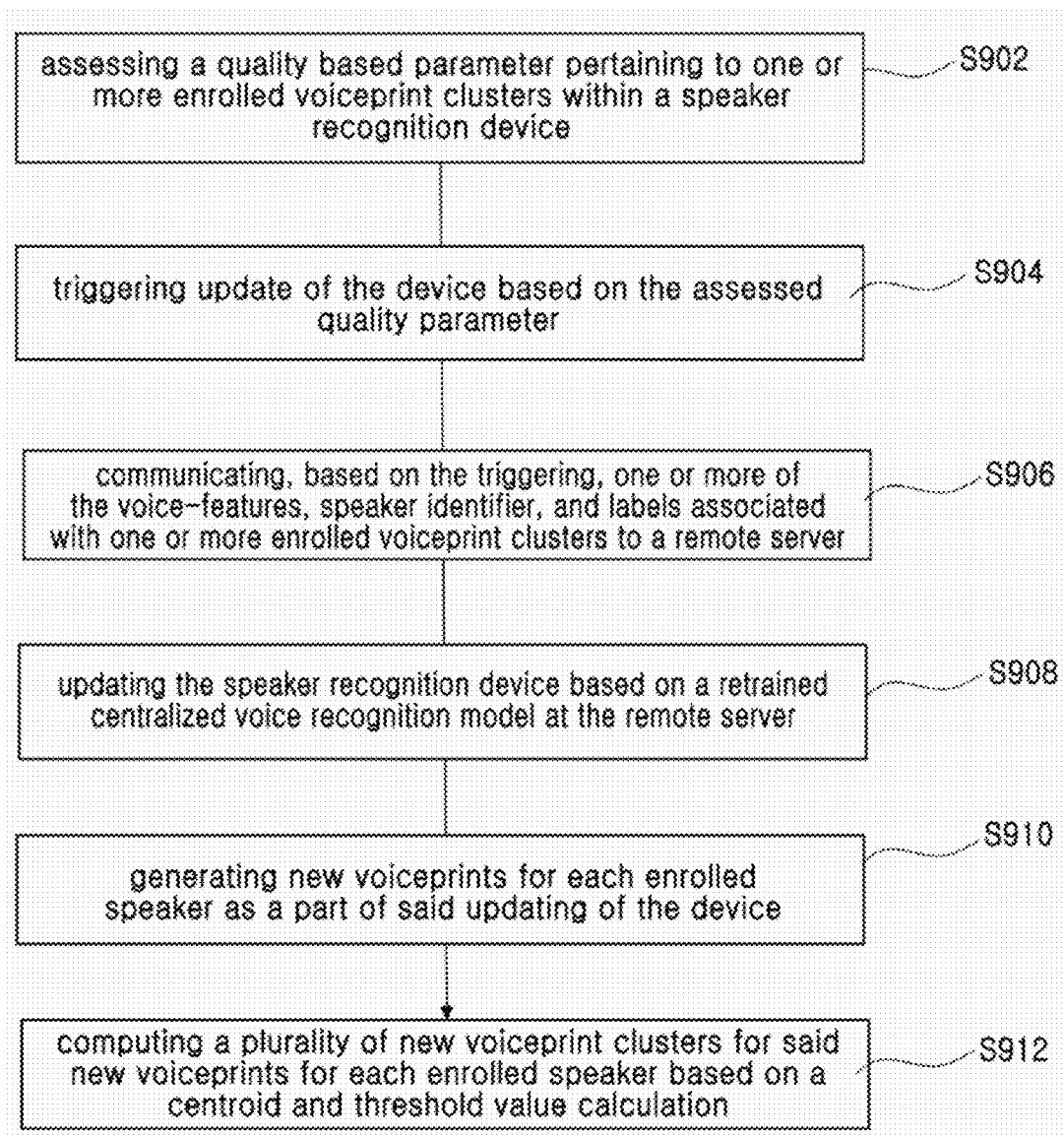
FIG. 9 illustrates method steps in accordance with another embodiment of the present disclosure.

FIG. 9 illustrates a method for updating a speaker recognition based computing device within a networking environment.

The method comprises assessing a quality based parameter pertaining to one or more enrolled voiceprint clusters within a speaker recognition device such that each of the enrolled voiceprint clusters is associated with a speaker identifier and labeled as one or more of: (a) normal voiceprint cluster (b) variability cluster (S902). The assessment of the quality parameter corresponds to cluster quality estimation (or identification or evaluation) in respect of the enrolled voiceprint clusters and determined by estimation of:

a) in respect of a first cluster (reference cluster), an average distance to all voiceprints included in the first cluster from a centroid of the first cluster;

b) in respect of a plurality of clusters, an average distance from the centroid of the first cluster to all voiceprints included in a second cluster (one cluster different from the first cluster among the plurality of clusters) (if the plurality of clusters are n clusters, the first cluster may obtain an average distance between clusters corresponding to each of n−1 clusters.); and c) an analysis based on the average distance from the centroid of the first cluster to all voiceprints included in the cluster closest to the first cluster and the average distance from the centroid of the first cluster to all voiceprints included in the first cluster (based on the first cluster, it indicates a degree of overlap between the voiceprint included in the first cluster and the voiceprint included in the closest cluster).

More specifically, based on cluster quality estimation results, the system 300 decides if local adaption (as depicted in FIGS. 7, 8A and 8B) or global model update is required for calculation of voiceprint clusters for unknown voice variability in case of false rejections, instead of the voiceprint clusters generated through the step 702. In an example, the global model update is required in respect of:

a) Embeddings resulting from environment noise are usually accommodated as a part of the formation of the voiceprint clusters. Accordingly, over some time, presence of a large number of voiceprint clusters comprising the ambient noise augments the probability of false acceptances.

b) Due to local adaption as depicted in the step 702, a substantial number of voiceprint clusters occupy space within the speaker enrollment DB. As a result, the variability clusters of one user starts overlapping with another speaker's cluster.

The conditional update to the server or the global model depends on the cluster quality of user's voiceprints with variations. Efficient cluster quality is to find out how well the clusters are separated. The "Cluster Quality Estimations approach" of step 902 for the user's voice data selection for the global model update is at least based on:

i) Estimation of the average distance from the centroid of the first cluster (reference cluster) to all cluster points included in the first cluster.

ii) Estimation of the average distance from the centroid of the first cluster to all cluster points included in the second cluster (one cluster different from the first cluster) (if the plurality of clusters are n, the first cluster is n−1) (if the plurality of clusters are n, the first cluster may obtain the average distance between clusters corresponding to each of n−1 clusters).

iii) Finding the closest cluster based on the first cluster.

iv) Analysis based on the average distance from the centroid of the first cluster to all cluster points included in the cluster closest to the first cluster and the average distance from the centroid of the first cluster to all cluster points included in the first cluster (based on the first cluster, it indicates a degree of overlap between the cluster point included in the first cluster and the cluster point included in the closest cluster).

Further, an update of the device is triggered based on the assessed quality parameter (S904). Based on the triggering, one or more of the voice features, speaker identifier, and labels associated with one or more enrolled voiceprint clusters are communicated to a remote server (S906). Relearning of a centralized voice recognition model at the remote server comprises relearning of a speaker recognition model. A voice clustering (or voiceprint clustering) model is relearned to thereby generate updated clusters and threshold based on the received voice features from the speaker recognition device. Based thereupon, a cluster map based on the updated speaker recognition model is created and the clustering module at the centralized server is updated.

The speaker recognition device (i.e., client) is updated based on the relearned centralized voice recognition model at the remote server (S908). More specifically, the updating of the speaker recognition device comprises accepting a model update request from the remote server and deleting the existing voiceprint clusters stored in speaker enrollment DB. In other examples, the updating of the speaker recognition device comprises shortlisting one or more of the speaker recognition device out of a plurality of speaker recognition devices connected to the remote server. The shortlisted set is defined by a particular region or a particular category of the device. The update of the shortlisted set of speaker recognition devices is triggered to thereby enable a regional update or a device category based update.

New voiceprints are generated for each enrolled speaker as a part of the updating of the device (S910). The new voiceprints are regenerated for each of the enrolled speakers based on the stored voice features of the enrolled users. Accordingly, a plurality of new voiceprint clusters are computed for the new voiceprints for each enrolled speaker based on a centroid and threshold value calculation (S912). Accordingly, a plurality of voice print clusters are formed in respect of the new voiceprints.

Figure 10:
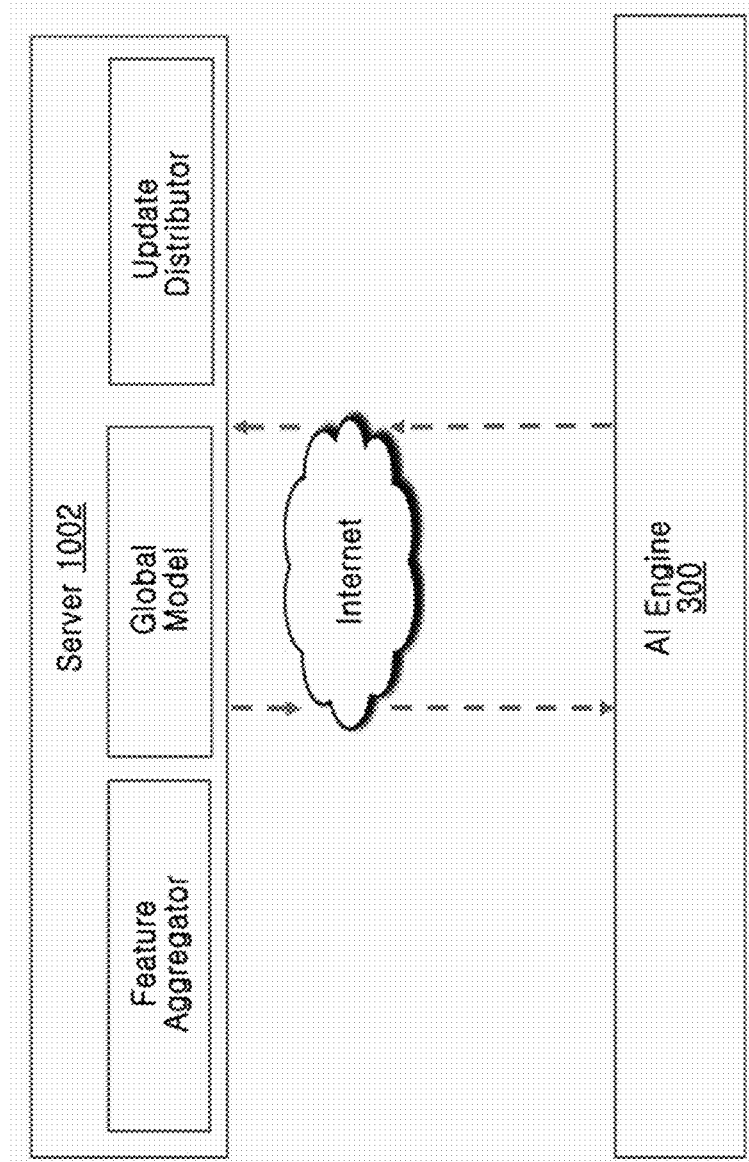
FIG. 10 illustrates an example sub-process in accordance with an embodiment of the present disclosure.

FIG. 10 illustrates a client server architecture comprising centralized remotely accessible server 1002 interacting with the AI engine 300. While the AI engine 300 executes the steps 902 to 912 of FIG. 9, the server 1002 undergoes relearning for communicating the global update back to the client device comprising the AI engine 300.

In an example, the AI engine 300 executes the "cluster quality estimation" as depicted in the step 902 for each cluster of users. An average distance Aci is calculated as:

$$Ac_i = \frac{\left(\sum_{k=1}^{n_i} |k - \text{centroid } i|\right)}{n_i}$$

Where, $i \in [1, 2, 3, 4, \ldots, n]$ $Ac_i$=Average distance of cluster $c_i$ (Average distance from a centroid of cluster ci to all data points (cluster points) included in cluster ci)

$n_i$=Number of data points in cluster i

|k−centroid i|=Distance of data points from centroid of $c_i$

If the average distance from the centroid p of cluster ci to all cluster points (data points) included in other clusters cj is $d(p,ci)_{cj}$, Bi may be defined as follows.

$Bi = \min(d(p,ci)_{cj})$

Bi may be used to find the closest cluster in the cluster ci. Quality index Qci can be defined as:

$$Qc_i = \frac{B_i - Aci}{\max(B_i, Aci)}$$

As a part of the operation of the decision module 306, a localized decomposition of cluster value of quality index Qci is evaluated. The quality index Qci may be a value indicating how far the cluster ci and the cluster closest to the cluster ci are separated. If Qci is closer to 1, the clusters are well separated and local adaptation depicted in FIG. 7 and FIGS. 8A and 8B is capable to handle voice variations. However, if Qci<0.5 (or a value which can be fine-tuned), then voice features are sent for global update as per step 904.

Figure 11A:
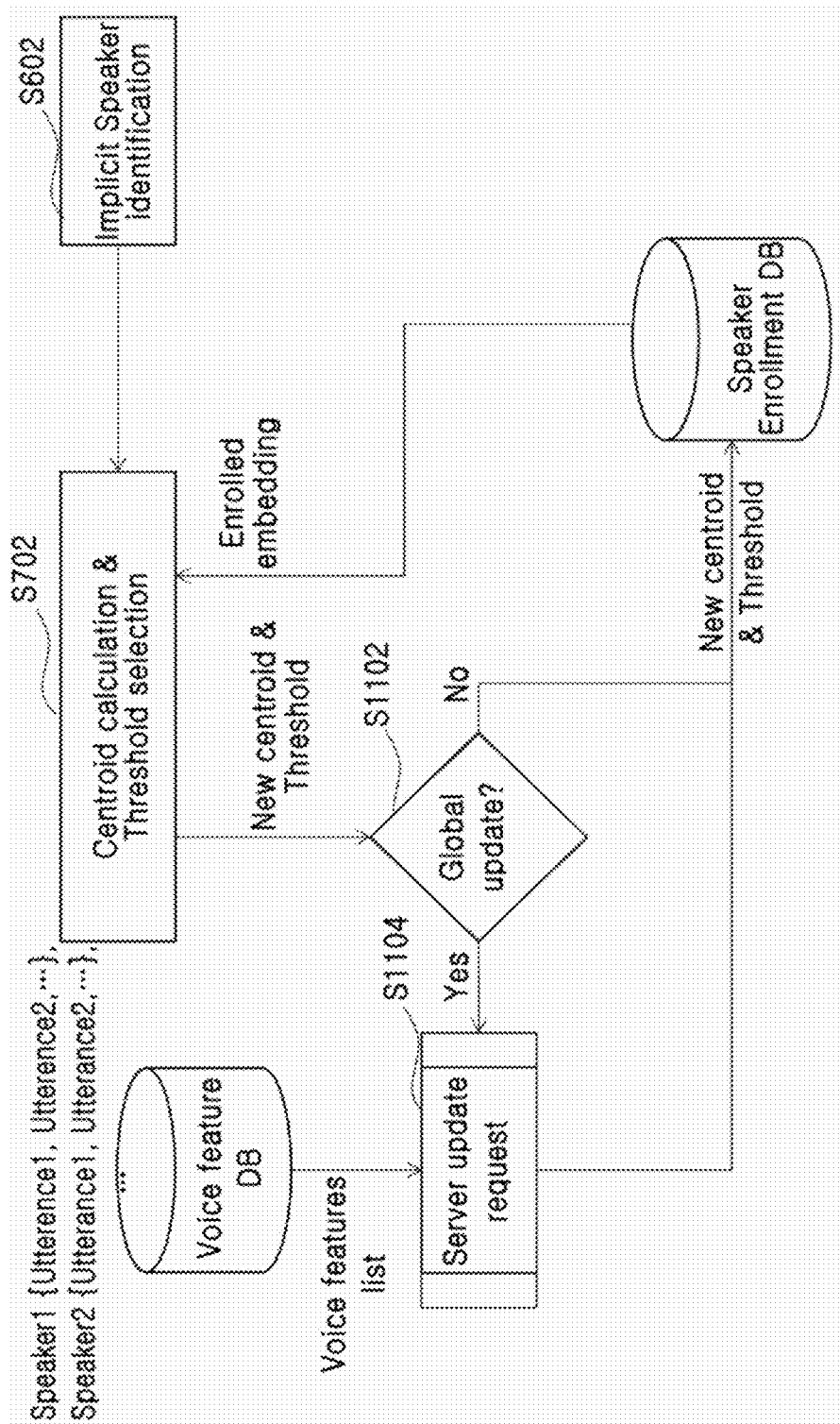

FIG. 11A illustrates conditional global update steps and thereby illustrates the operation of the steps 904 to 906 by the AI engine 300 operationally interacting with the server 1002. As may be understood, the data communication in respect of global update involves sharing of voice features instead of sharing voiceprint data and thereby assures confidentiality.

At step 1102, the decision module 306 decides the implementation of global or local update. In the case of a local update, the new centroid and cluster calculated in FIG. 7 are sent to the speaker enrollment DB. In case of a global update, the control transfers to step 1104.

At step 1104, the voice features are extracted on a device incorporating the AI engine 300 and communicated to the server 1002 to mitigate privacy concerns. More specifically, the voice features of all voice samples available in the speaker enrolled DB are shared with the server.

As a part of relearning, the server 1002 collects all the voice features and filters the outliers. The global model for speaker recognition is relearned with collected data from various clients. The voice clustering model is also relearned with collected data from various clients to get improved clusters (with refined thresholds) for existing variations as well as identify new variation clusters (if any). A new cluster delta map is created using the updated/new clustering module and the updated speaker recognition model. On training completion, the updated global model and cluster map are pushed back to all clients for speaker recognition performance improvement. The client device comprising the AI engine 300 receives the new model update notification and can accept, reject or defer the update installation.

Figure 11B:
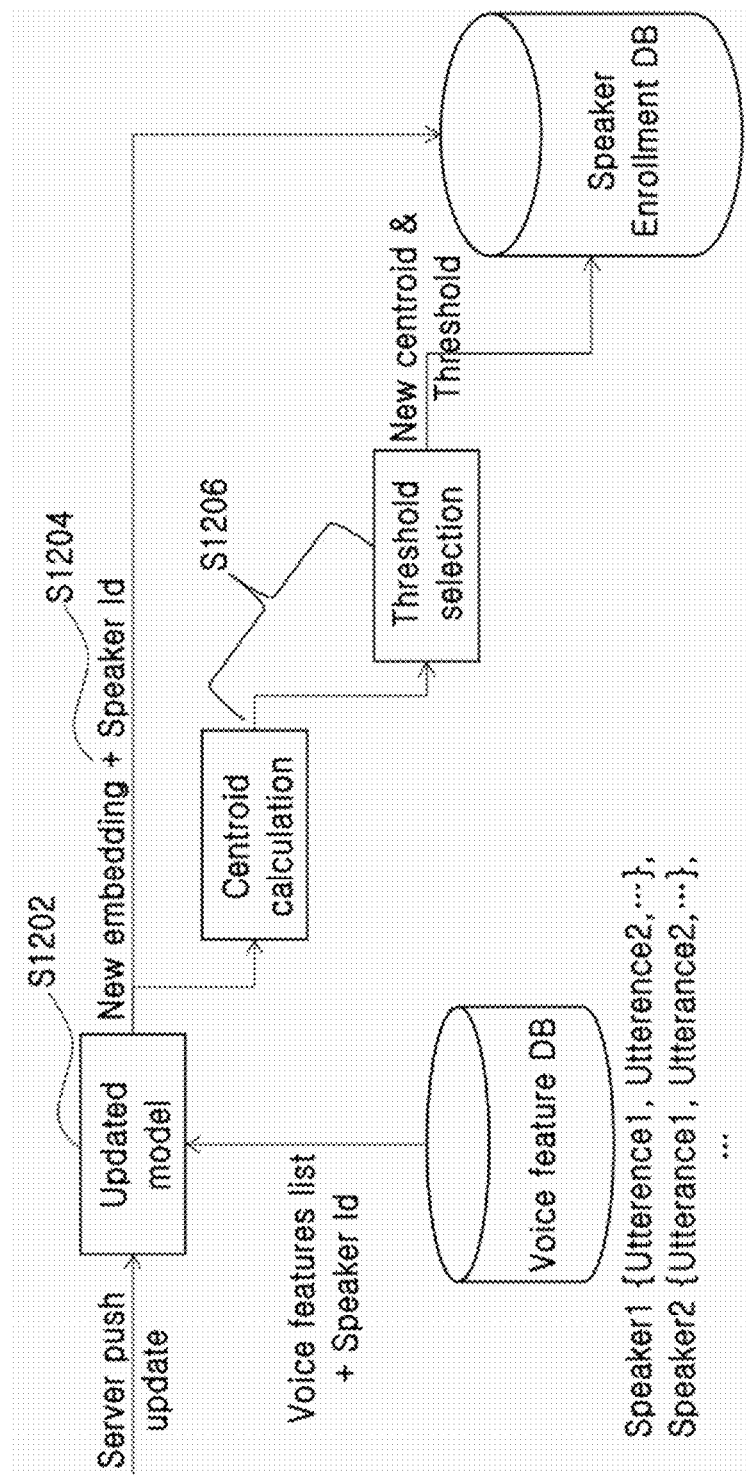

FIG. 11B illustrates an auto-enrolment phase with respect to the AI engine 300 within the client device and corresponds to the steps 908 to 912 of FIG. 9.

At step 1202, the global model update at the client side initiates with the discarding of all the voiceprints, centroids and thresholds stored in the speaker enrolment DB.

At step 1204, the client device re-generates the voiceprints for all enrolled voice samples by automatically using stored voice features of enrolled users. This eliminates need for a user to re-enroll on model update and ensures a hassle-free user interaction.

At step 1206, upon generation of new voiceprints, centroid and threshold are calculated for these new voiceprints and stored in the speaker enrolments DB.

Figure 12A:
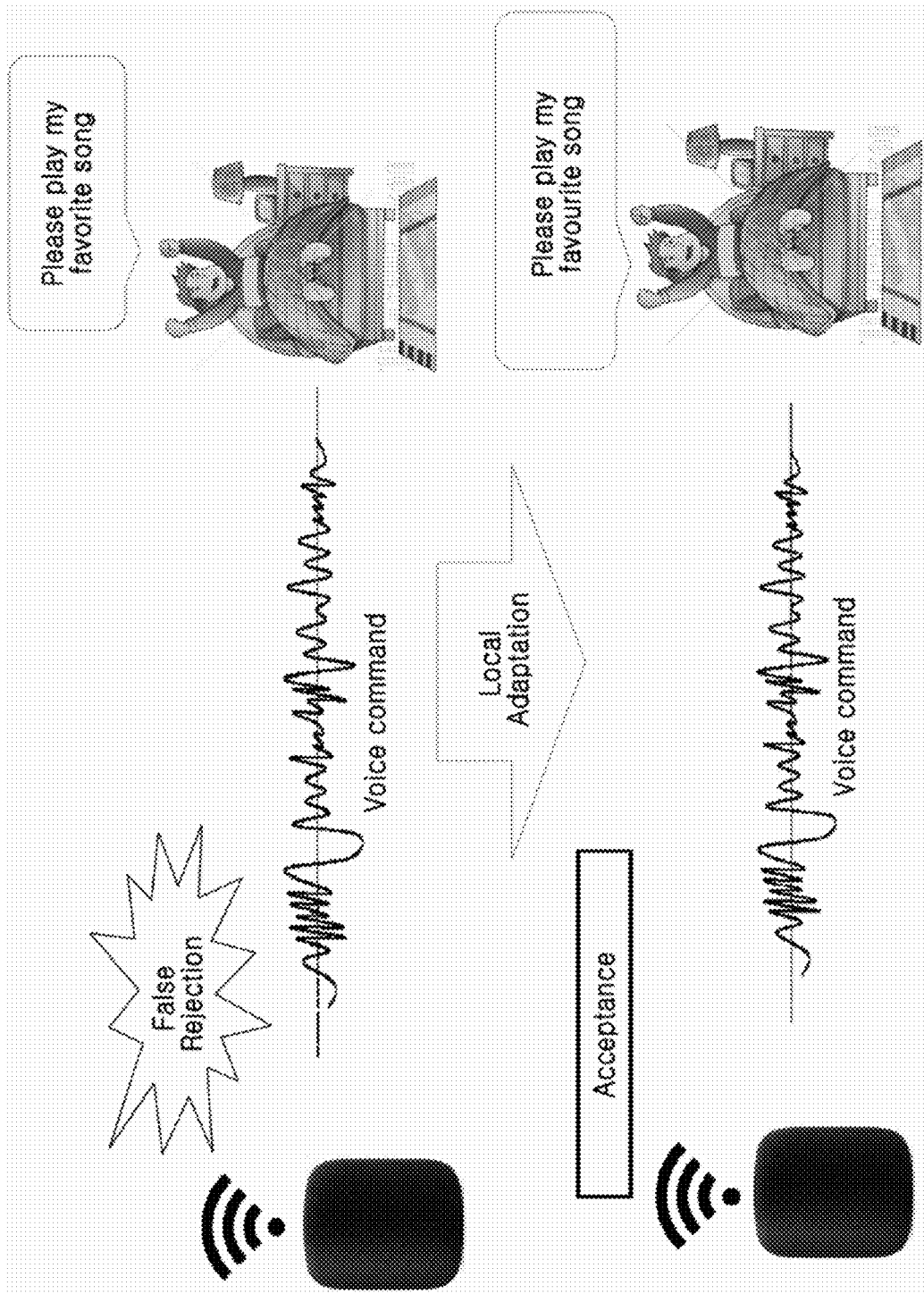
FIGS. 12A and 12B illustrate example voice variability scenarios considered in respect of an embodiment of the present disclosure.
Figure 12B:
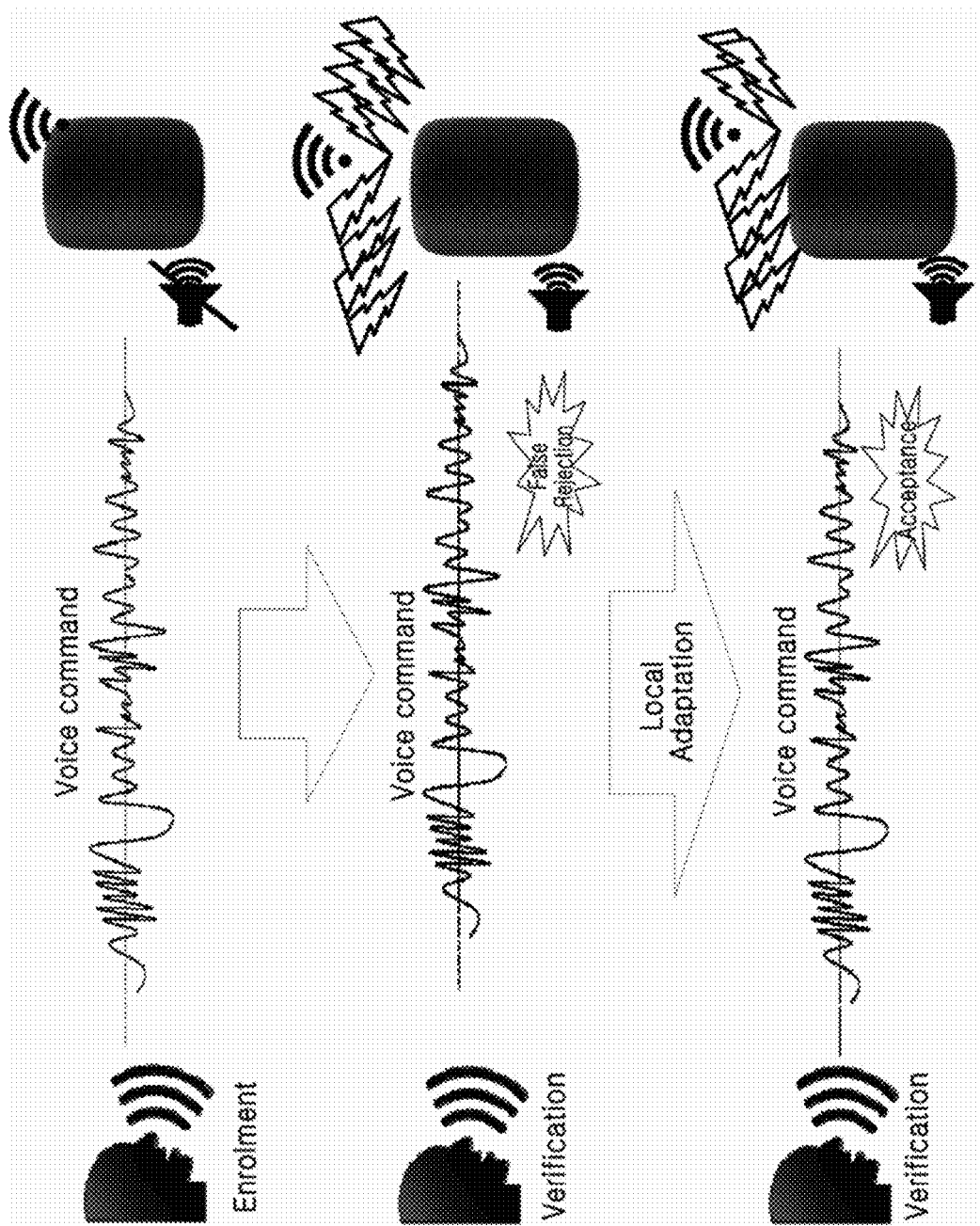

FIGS. 12A and 12B illustrate individual voice variation scenario and its handling in accordance with an embodiment of the present disclosure. FIG. 12A illustrates "Croaky morning voice" scenario. "Morning voice," or the deeper voice is experienced after getting up in the morning. State of the art systems falsely reject voice command at this time of the day. With the proposed approach of voice variability detection and local adaptation of user's voiceprints, these false rejections can be avoided/eliminated. FIG. 12B detects the "Environmental noise" scenario. Usually, during the enrolment phase, there is no sound on the device (low background noise). But during verification phase, there may be song playing on the device, other background noises also may be present. This mismatch in enrolment and verification environment leads to false detection. With the proposed approach, various noisy conditions will be accommodated over time and false rejections substantially reduce.

Figure 13:
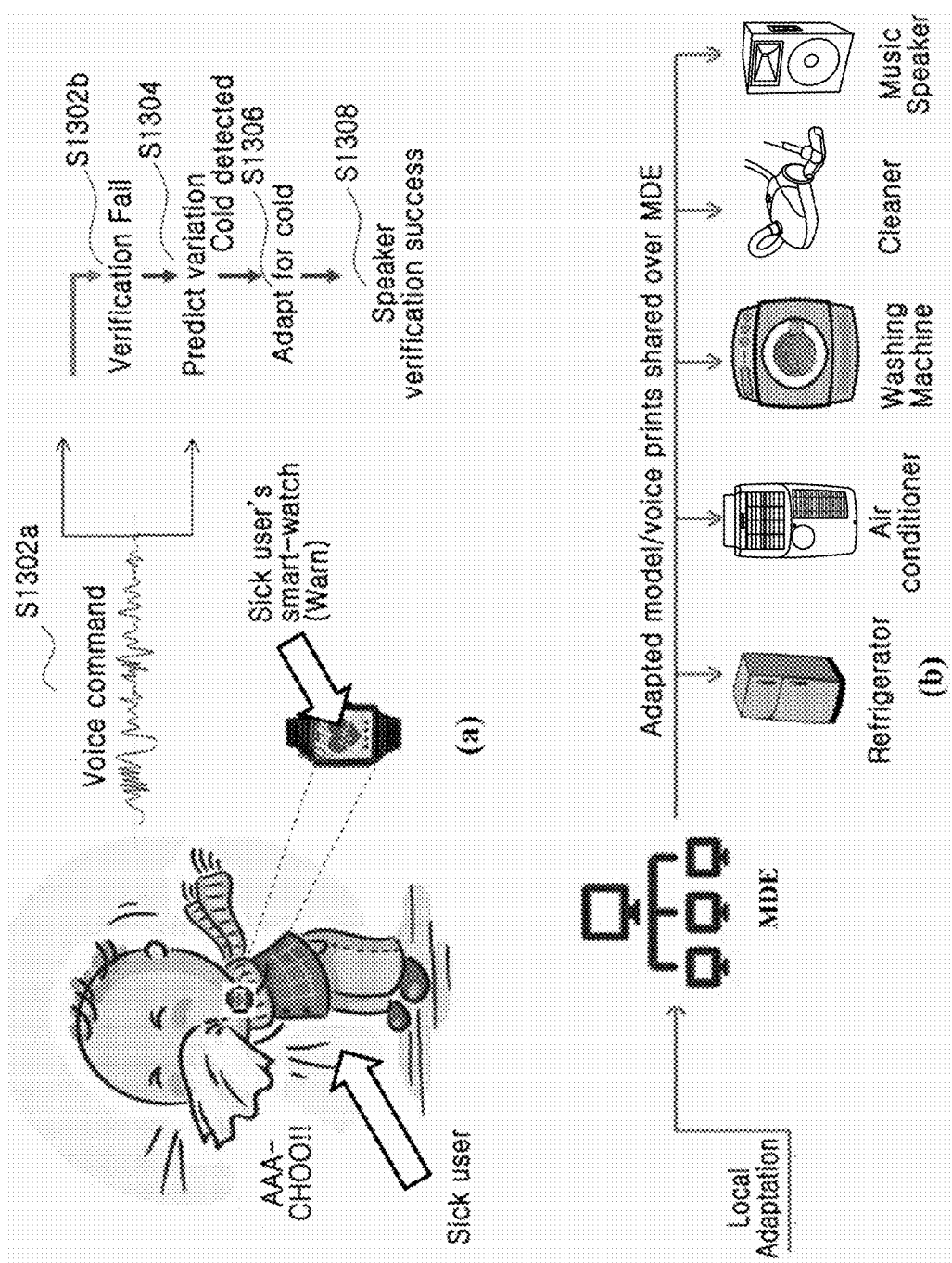
FIG. 13 illustrates an example implementation in accordance with an embodiment of the present disclosure.

FIG. 13 illustrates another voice variation scenario. (a) of FIG. 13 illustrates a scenario wherein a user is suffering from cold due to which there is variation in his voice. When the user 1 attempts to access his account with voice command (S1302a), speaker verification fails at the device end because of varied voice ("false rejection") (S1302b). To prevent this "false rejection", the device collects health status information from speaker's wearable devices (if available) along with voice features extracted from the current utterance and provides the same as input to the identification module 310 to predict variability condition. Based on inputs, the module 310 detects that the user is suffering from cold (S1304) and adapts centroid and threshold values accordingly (S1306). With the adapted centroid and threshold values, speaker verification is successful (S1308) and the user is granted access. (b) of FIG. 13 illustrates an extended scenario wherein adapted voiceprints, centroid and threshold are shared via an MDE server to other devices in a home environment. In addition to VPA, the user tries to use voice command to control operation on the refrigerator. As adaptation is applied, this time 'user' is successfully identified by the system and access granted to control refrigerator operation. After some time, the user tries to use voice command to play air conditioner. Adapted models/voiceprints are shared to air conditioner and adaptation is applied on air conditioner also. The user is successfully identified by the system and access granted to control operations of air conditioner. The similar rationale may be applicable for other devices, e.g., TV, robotic cleaner, music speaker, etc.

Figure 14:
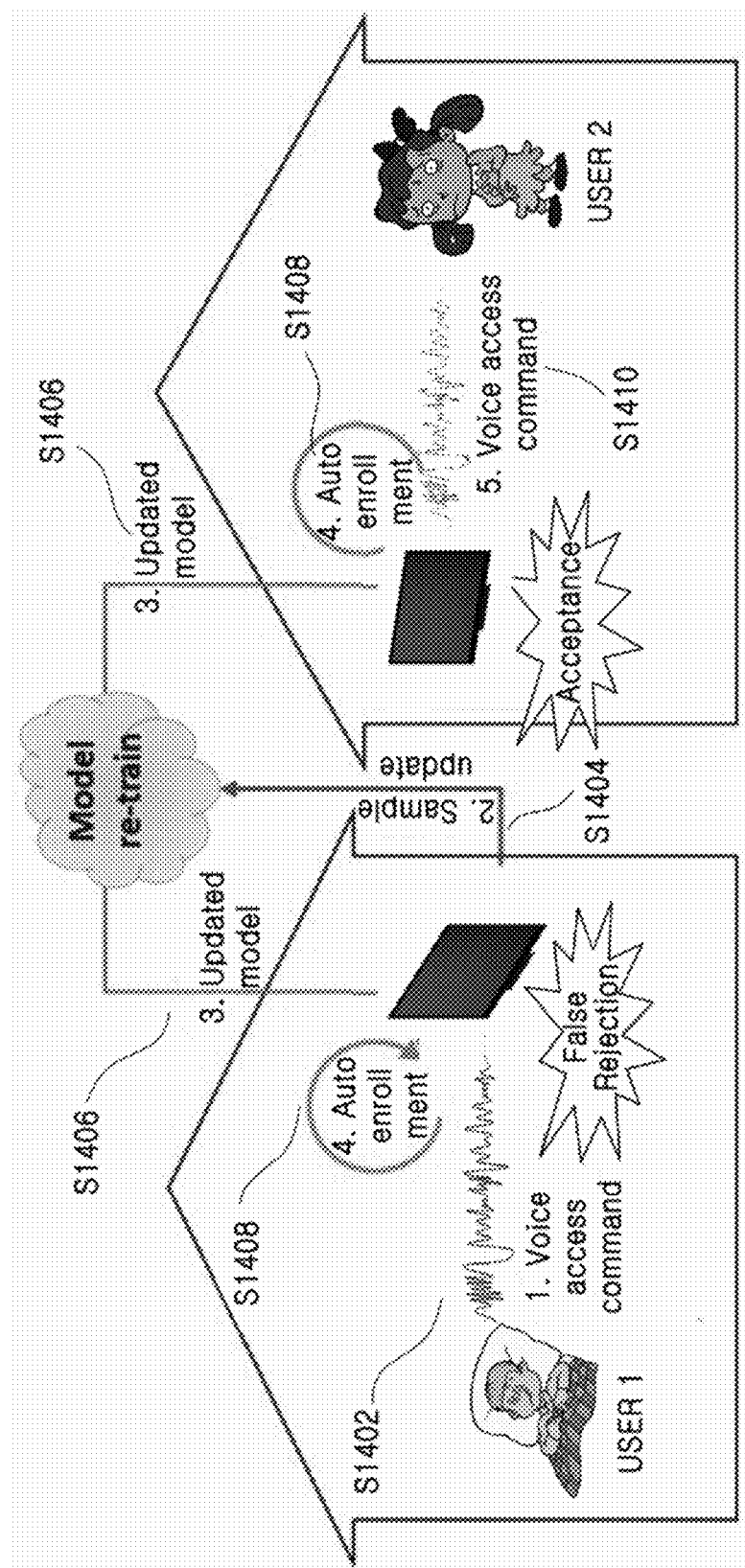
FIG. 14 illustrates another example implementation in accordance with an embodiment of the present disclosure.

FIG. 14 illustrates a global update based scenario and deals with a scenario pertaining to health condition (cold/sore throat, etc.). User 1 is suffering from cold due to which there is slight variation in his voice. User 1 attempts to access his account with voice command, but speaker identification fails (S1402) at the device end because of varied voice ("false rejection"). The device identifies User 1 via secondary methods (i.e., via the module 310) and extracts features from varied voice and uploads (S1404) to a server. Global model is updated when following two major conditions are satisfied:

Embedding is quite far from their enrolled cluster and another added cluster does not help improving the system performance; and One of the clusters starts overlapping with another cluster. Once cluster starts overlapping with other clusters, the local update needs to stop as it will start to degrade the performance of the system.

The global model is relearned using new data collected from various devices and the updated model is pushed back to devices (S1406). On global model update, auto enrolment is done with user's stored voice samples (S1408). Now, User 2 who is also suffering from cold tries to access her account using voice command. This time the device identifies her even with her changed voice and grants her access (S1410). The same holds applicable for user 1 as well.

Further, the present global update based scenario may be also appropriate for a regional update mechanism. Since common health conditions like flu, cold, soar-throat, etc. are seasonal, many people are affected by these common health conditions in a region/geographical location during a season (winter, rainy season, etc.). Due to a sudden increase in number of people suffering from these health conditions in that region during a season, voice authentication system performance takes a hit with a rapid increase in false rejection cases. These regions can be identified by rate of false rejections and a region-wise global model re-learning and update can be triggered to quickly handle these false rejection cases without compromising system performance in un-affected areas/regions.

Figure 15:
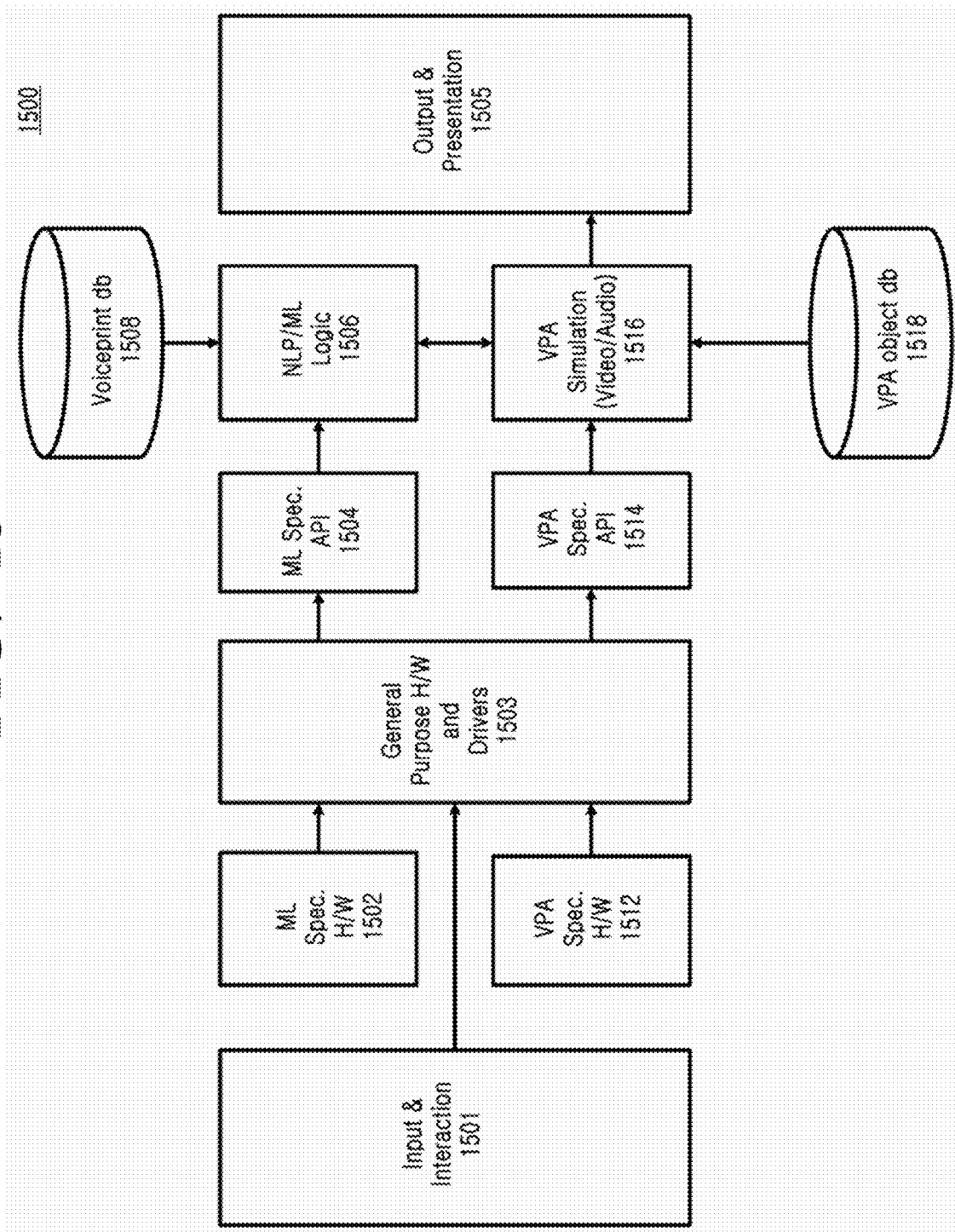
FIG. 15 illustrates another system architecture implementing various modules and sub-modules in accordance with the implementation depicted in FIGS. 3 and 9.

FIG. 15 illustrates a representative architecture 1500 to provide tools and development environment described herein for a technical realization of the implementation in FIG. 3 and FIG. 9 through a virtual personal assistance (VPA) based computing device. FIG. 15 is merely a non-limiting example, and it will be appreciated that many other architectures may be implemented to facilitate the functionality described herein. The architecture may be executing on hardware such as a computing machine (computing device, 1600) of FIG. 16 that includes, among other things, processors, memory, and various application-specific hardware components.

The architecture 1500 may include an operating-system, libraries, frameworks or middleware. The operating system may manage hardware resources and provide common services. The operating system may include, for example, a kernel, services, and drivers defining a hardware interface layer. The drivers may be responsible for controlling or interfacing with the underlying hardware. For instance, the drivers may include display drivers, camera drivers, Bluetooth® drivers, flash memory drivers, serial communication drivers (e.g., Universal Serial Bus (USB) drivers), Wi-Fi® drivers, audio drivers, power management drivers, and so forth depending on the hardware configuration.

A hardware interface layer includes libraries which may include system libraries such as file-system (e.g., C standard library) that may provide functions such as memory allocation functions, string operation functions, mathematic functions, and the like. In addition, the libraries may include API libraries such as audio-visual media libraries (e.g., multi-media data libraries to support presentation and operation of various media format such as MPEG4, H.264, MP3, AAC, AMR, JPG, PNG), database libraries (e.g., SQLite that may provide various relational database functions), web libraries (e.g. WebKit that may provide web browsing functionality), and the like.

A middleware may provide a higher level common infrastructure such as various graphic user interface (GUI) functions, high-level resource management, high level location services, and so forth. The middleware may provide a broad spectrum of other APIs that may be utilized by the applications or other software components/modules, some of which may be specific to a particular operating system or platform.

The term "module" used in this disclosure may refer to a certain unit that includes one of hardware, software and firmware or any combination thereof. The module may be interchangeably used with unit, logic, logical block, component, or circuit, for example. The module may be the minimum unit, or part thereof, which performs one or more particular functions. The module may be formed mechanically or electronically. For example, the module disclosed herein may include at least one of ASIC (Application-Specific Integrated Circuit) chip, FPGAs (Field-Programmable Gate Arrays), and programmable-logic device, which have been known or are to be developed.

Further, the architecture 1500 depicts an aggregation of VPA based mechanisms and ML/NLP (Machine Learning/Natural Language Processing) based mechanism in accordance with an embodiment of the present disclosure. A user-interface defined as input and interaction 1501 refers to overall input. It can include one or more of the following—touch screen, microphone, camera, etc. A first hardware module 1502 depicts specialized hardware for ML/NLP based mechanisms. In an example, the first hardware module 1502 comprises one or more of neural processors, FPGA, DSP, GPU, etc.

A second hardware module 1512 depicts specialized hardware for executing the VPA device-related audio and video simulations. ML/NLP based frameworks and APIs 1504 correspond to the hardware interface layer for executing the ML/NLP logic 1506 based on the underlying hardware. In an example, the frameworks may be one or more or the following—Tensorflow, Café, NLTK, GenSim, ARM Compute, etc. VPA simulation frameworks and APIs 1514 may include one or more of—VPA Core, VPA Kit, Unity, Unreal, etc.

A database 1508 depicts a pre-trained voice feature database. The database 1508 may be remotely accessible through cloud by the ML/NLP logic 1506. In other examples, the database 1508 may partly reside on cloud and partly on-device based on usage statistics.

Another database 1518 refers to the speaker enrollment DB or the voice feature DB that will be used to authenticate and respond to the user. The database 1518 may be remotely accessible through cloud. In other example, the database 1518 may partly reside on the cloud and partly on-device based on usage statistics.

A rendering module 1505 is provided for rendering audio output and triggering further utility operations as a result of user authentication. The rendering module 1505 may be manifested as a display, touch screen, monitor, speaker, projection screen, etc.

Figure 16:
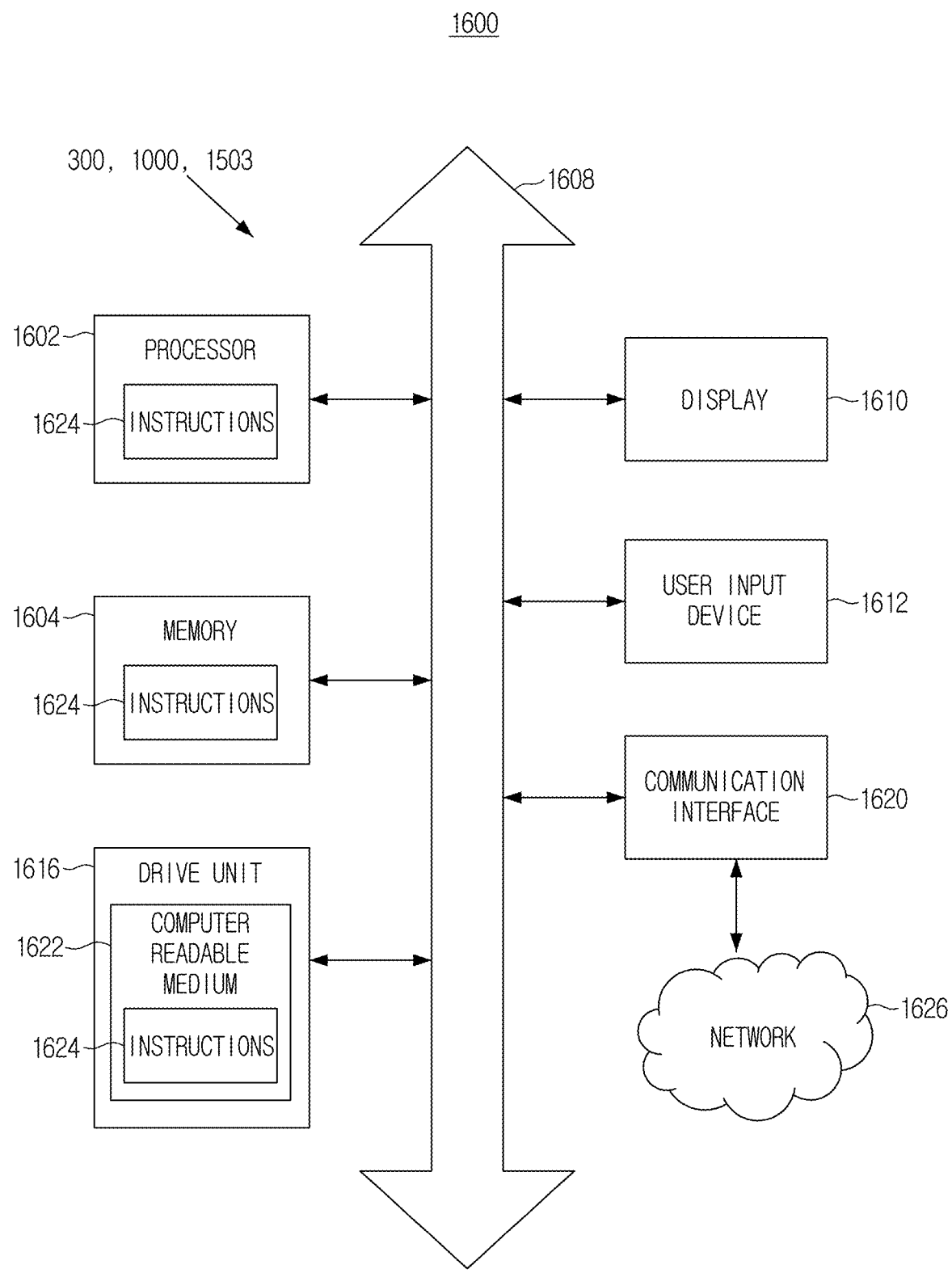
FIG. 16 illustrates a computing device based implementation in accordance with an embodiment of the present disclosure.

A general-purpose hardware and driver module 1503 corresponds to the computing device (computing system, 1600) as referred in FIG. 16 and instantiates drivers for the general purpose hardware units as well as the application-specific units (1502, 1512).

In an example, the NLP/ML mechanism and VPA simulations underlying the present architecture 1500 may be remotely accessible and cloud-based, thereby being remotely accessible through a network connection. A computing device such as a VPA device may be configured for remotely accessing the NLP/ML modules and simulation modules may comprise skeleton elements such as a microphone, a camera a screen/monitor, a speaker, etc.

Further, at least one of the plurality of modules 302 to 310 of FIG. 3 may be implemented through AI based on an ML/NLP logic 1506. A function associated with AI may be performed through the nonvolatile memory, the volatile memory, and the processor constituting the first hardware module 1502, i.e., specialized hardware for ML/NLP based mechanisms. The processor may include one or more processors. At this time, one or more processors may be a general purpose processor, such as a central processing unit (CPU), an application processor (AP), or the like, a graphics-only processing unit such as a graphics processing unit (GPU), a visual processing unit (VPU), and/or an AI-dedicated processor such as a neural processing unit (NPU). The above described processors collectively correspond to the processor 1602 of FIG. 16.

The one or more processors control the processing of the input data in accordance with a predefined operating rule or artificial intelligence (AI) model stored in the nonvolatile memory and the volatile memory. The predefined operating rule or artificial intelligence model is provided through training or learning.

Here, being provided through learning means that, by applying a learning logic/technique to a plurality of learning data, a predefined operating rule or AI model of a desired characteristic is made. The learning may be performed in a device (i.e. the architecture 1500 or the computing device (computing system 1600) itself in which AI according to an embodiment is performed, and/or may be implemented through a separate server/system.

The AI model may consist of a plurality of neural network layers. Each layer has a plurality of weight values, and performs a layer operation through calculation of a previous-layer and an operation of a plurality of weights. Examples of neural networks include, but are not limited to, convolutional neural network (CNN), deep neural network (DNN), recurrent neural network (RNN), restricted Boltzmann Machine (RBM), deep belief network (DBN), bidirectional recurrent deep neural network (BRDNN), generative adversarial networks (GAN), and deep Q-networks.

The ML/NLP logic 1506 performs a method for training a predetermined target device (for example, a robot) using a plurality of learning data to cause, allow, or control the target device to make a determination or prediction. Examples of learning techniques include, but are not limited to, supervised learning, unsupervised learning, semi-supervised learning, or reinforcement learning.

FIG. 16 shows yet another exemplary implementation in accordance with the embodiment, and yet another typical hardware configuration of the system 300, 1000, 1503 in the form of the computer system 1600 is shown. The computer system 1600 can include a set of instructions that can be executed to cause the computer system 1600 to perform any one or more of the methods disclosed. The computer system 1600 may operate as a standalone device or may be connected, e.g., using a network, to other computer systems or peripheral devices.

In a networked deployment, the computer system 1600 may operate in the capacity of a server or as a client user computer in a server-client user network environment, or as a peer computer system in a peer-to-peer (or distributed) network environment. The computer system 1600 can also be implemented as or incorporated across various devices, such as a VR device, personal computer (PC), a tablet PC, a personal digital assistant (PDA), a mobile device, a palmtop computer, a communications device, a web appliance, or any other machine capable of executing a set of instructions (sequential or otherwise) that specify actions to be taken by that machine. Further, while a single computer system 1600 is illustrated, the term "system" shall also be taken to include any collection of systems or sub-systems that individually or jointly execute a set, or multiple sets, of instructions to perform one or more computer functions.

The computer system 1600 may include a processor 1602, e.g., a central processing unit (CPU), a graphics processing unit (GPU), or both. The processor 1602 may be a component in a variety of systems. For example, the processor 1602 may be part of a standard personal computer or a workstation. The processor 1602 may be one or more general processors, digital signal processors, application specific integrated circuits, field programmable gate arrays, servers, networks, digital circuits, analog circuits, combinations thereof, or other now known or later developed devices for analyzing and processing data. The processor 1602 may implement a software program, such as code generated manually (i.e., programmed).

The computer system 1600 may include a memory 1604, such as a memory 1604 that can communicate via a bus 1608. The memory 1604 may include, but is not limited to, computer readable storage media such as various types of volatile and nonvolatile storage media, including but not limited to random access memory, read-only memory, programmable read-only memory, electrically programmable read-only memory, electrically erasable read-only memory, flash memory, magnetic tape or disk, optical media and the like. In one example, the memory 1604 includes a cache or random access memory for the processor 1602. In alternative examples, the memory 1604 is separate from the processor 1602, such as a cache memory of a processor, the system memory, or other memory. The memory 1604 may be an external storage device or database for storing data. The memory 1604 is operable to store instructions executable by the processor 1602. The functions, acts or tasks illustrated in the figures or described may be performed by the programmed processor 1602 executing the instructions stored in the memory 1604. The functions, acts or tasks are independent of the particular type of instructions set, storage media, processor or processing strategy and may be performed by software, hardware, integrated circuits, firmware, micro-code and the like, operating alone or in combination. Likewise, processing strategies may include multiprocessing, multitasking, parallel processing and the like.

As shown, the computer system 1600 may or may not further include a display unit 1610, such as a liquid crystal display (LCD), an organic light emitting diode (OLED), a flat panel display, a solid state display, a cathode ray tube (CRT), a projector, or other now known or later developed display device for outputting determined information. The display 1610 (or display unit) may act as an interface for the user to see the functioning of the processor 1602, or specifically as an interface with the software stored in the memory 1604 or in the drive unit 1616.

Additionally, the computer system 1600 may include an input device 1612 configured to allow a user to interact with any of the components of system 1600. The computer system 1600 may also include a disk or optical drive unit 1616. The disk drive unit 1616 may include a computer-readable medium 1622 in which one or more sets of instructions 1624, e.g. software, can be embedded. Further, the instructions 1624 may embody one or more of the methods or logic as described. In a particular example, the instructions 1624 may reside completely, or at least partially, within the memory 1604 or the processor 1602 during execution by the computer system 1600.

The present disclosure contemplates a computer-readable medium that includes instructions 1624 or receives and executes instructions 1624 responsive to a propagated signal so that a device connected to a network 1626 can communicate voice, video, audio, images or any other data over the network 1626. Further, the instructions 1624 may be transmitted or received over the network 1626 via a communication port or interface 1620 or using a bus 1608. The communication port or interface 1620 may be a part of the processor 1602 or maybe a separate component. The communication port or interface 1620 may be created in software or maybe a physical connection in hardware. The communication port or interface 1620 may be configured to connect with the network 1626, external media, the display 1610, or any other components in the system 1600, or combinations thereof. The connection with the network 1626 may be a physical connection, such as a wired Ethernet connection or may be established wirelessly as discussed later. Likewise, the additional connections with other components of the system 1600 may be physical or may be established wirelessly. The network 1626 may alternatively be directly connected to the bus 1608.

The network 1626 may include wired networks, wireless networks, Ethernet AVB networks, or combinations thereof. The wireless network may be a cellular telephone network, an 802.11, 802.16, 802.20, 802.1Q or WiMax network. Further, the network 1626 may be a public network such as the Internet, a private network such as an intranet, or combinations thereof, and may utilize a variety of networking protocols now available or later developed including, but not limited to, TCP/IP based networking protocols. The system is not limited to operation with any particular standards and protocols. For example, standards for Internet and other packet switched network transmission (e.g., TCP/IP, UDP/IP, HTML, HTTP) may be used.

At least based on the preceding description, the present disclosure facilitates an automatic classification of voice variability wherein the speaker's voice variability is detected automatically and an appropriate threshold value is chosen based on experimental results. Since an automatic curation of voice data is provided based on the false rejection of person's voice identity, the device will identify the person implicitly using various sensors, usage patterns, user behavior, etc. and label the voice sample. An adaptive speaker model is provided to generate a new centroid of user's voiceprints by including varied voice samples locally. A conditional update (re-learning) of global model is provided with curated voice features extracted locally on the device and shared with the server, thereby eliminating privacy concerns and rendering updated model to the device. Last but not the least, auto enrolments of user is executed based on stored voice features on global model update for hassle-free user interaction.

While specific language has been used to describe the disclosure, any limitations arising on account of the same are not intended. As would be apparent to a person in the art, various working modifications may be made to the method in order to implement the inventive concept as taught herein.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein.

Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component of any or all the claims.

Figure 17:
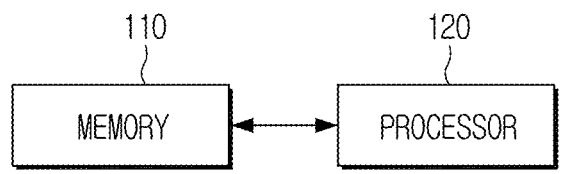
FIG. 17 is a block diagram illustrating an electronic apparatus according to an embodiment of the present disclosure.

FIG. 17 is a block diagram illustrating an electronic apparatus according to an embodiment.

Referring to FIG. 17, the electronic apparatus 100 may include a memory 110 and a processor 120. In addition, the electronic apparatus 100 may include at least one of a communication interface (not shown), a user interface (not shown), an input/output interface (not shown), a sensor (not shown), or a display (not shown).

The electronic apparatus 100 according to various embodiments may include at least one of, for example, a smart phone, a tablet PC, a mobile phone, a desktop PC, a laptop PC, a PDA, and a portable multimedia player (PMP). In some embodiments, the electronic apparatus 100 may include at least one of, for example, a television, a digital video disk (DVD) player, and a media box (e.g., Samsung HomeSync™, Apple TV™, or Google TV™).

The memory 110 may be implemented as an internal memory such as a ROM (e.g., an electrically erasable programmable read-only memory (EEPROM)) a RAM, or the like included in the processor 120, or may also be implemented as a memory separate from the processor 120. In this case, the memory 110 may be implemented in a form of a memory embedded in the electronic apparatus 100 or may be implemented in a form of a memory that is detachable to the electronic apparatus 100 according to a purpose of data storage. For example, in the case of data for driving the electronic apparatus 100, it may be stored in a memory embedded in the electronic apparatus 100, and in the case of data for an extended function of the electronic apparatus 100, the electronic apparatus 100 may be stored in a memory detachable to the electronic apparatus 100.

Meanwhile, in the case of a memory embedded in the electronic apparatus 100, a volatile memory (e.g., dynamic RAM (DRAM), static RAM (SRAM), or synchronous dynamic RAM (SDRAM)), a non-volatile memory (e.g., one time programmable ROM (OTPROM)), programmable ROM (PROM), erasable and programmable ROM (PROM), electrically erasable and programmable ROM (EEPROM), mask ROM, flash ROM, flash memory (e.g. NAND flash or NOR flash, etc.)), a hard drive, or a solid state drive (SSD), and in the case of the memory that is detachable to the electronic apparatus 100, it may be implemented in a form of an external memory that may be connected to a memory card (e.g., compact flash (CF), secure digital (SD), micro secure digital (Micro-SD), mini secure digital (Mini-SD), extreme digital (xD), multi-media card (MMC), etc., external memory that can be connected to a USB port (e.g., USB memory) and the like.

The memory 110 may store at least one pre-registered voiceprint and a first voiceprint cluster including at least one pre-registered voiceprint.

The voiceprint may refer to a unique voice feature of a user, and may be used as user identification information. The voiceprint may be obtained based on voice data, and since the voiceprint corresponding to the user is determined, the voiceprint may be different for each user. In addition, a plurality of voiceprints may be included for each user according to the user's speech pattern. For example, there may be a plurality of voiceprints corresponding to the user. Here, the plurality of voiceprints may be grouped according to certain criteria, and it may be defined as one cluster voiceprint by enclosing the at least one voiceprint. Accordingly, when the user speaks, the electronic apparatus 100 may identify a voiceprint cluster corresponding to the user's utterance, and identify whether a voiceprint corresponding to the user's utterance exists among voiceprints included in the identified voiceprint cluster.

The processor 120 may perform an overall control operation of the electronic apparatus 100. Specifically, the processor 120 functions to control the overall operation of the electronic apparatus 100.

The processor 120 may be implemented as a digital signal processor (DSP), a microprocessor, or a time controller (TCON) that processes digital signals, but is not limited thereto, and the processor 120 may include one or more among a central processing unit (CPU), microcontroller unit (MCU), micro processing unit (MPU), controller, application processor (AP), graphics-processing unit (GPU), or communication processor (CP), an ARM processor, or may be defined in a corresponding term. In addition, the processor 120 may be implemented as a system on chip (SoC) with a built-in processing algorithm, and a large scale integration (LSI), and may be implemented as a Field Programmable gate array (FPGA). In addition, the processor 120 may perform various functions by executing the computer-executable instructions stored in memory 110.

When a user recognition command is received, the processor 120 may acquire information of time (i.e., time information) at which the user recognition command is received, and may change at least one pre-stored voiceprint included in the first voiceprint cluster (or first cluster), and based on the at least changed voiceprint, generate a second voiceprint cluster (or second cluster), and based on the user's utterance being received, based on the first voiceprint cluster and the second voiceprint cluster, recognize a user's recognition with respect to the received user's utterance.

The user recognition command may refer to a predetermined event being recognized. The pre-determined event may be an action of a user selecting a home menu or an action of accessing a specific application.

The processor 120 may obtain time information at which the user recognition command is received. Further, the processor 120 may obtain time information (i.e., time information) at which the first voiceprint cluster is generated and stored in the memory. Further, the processor 120 may compare time information at which the first voiceprint cluster is generated and time information at which the user recognition command is received. If a difference between the time information at which the first voiceprint cluster is generated and the time information at which the user recognition command is received is large (e.g., more than three years), a person's voice may be changed, and thus misrecognition may occur. For example, if the user is a teenager in the changing age, he or she may have a different voice from the pre-registered voiceprint as time passes. Therefore, the processor 120 may need to change the pre-registered voiceprint and a process to change the voiceprint cluster based on the time information.

The processor 120 may obtain a difference value between the time information when the first voiceprint cluster is generated and the time information at which the user recognition command is received. In addition, the processor 120 may generate a second voiceprint cluster based on the obtained difference value.

Specifically, as the obtained difference value increases, the processor 120 may generate the second voiceprint cluster by significantly changing the information included in the first voiceprint cluster.

The processor 120 may change the voiceprint data itself included in the first voiceprint cluster, or change a first center value and a first threshold value corresponding to the first voiceprint cluster.

Further, the processor 120 may perform a user recognition function (or operation) on the received user's utterance based on the first voiceprint cluster (pre-stored) and the second voiceprint cluster (newly generated).

Since the processor 120 considers both past time information (time information at which the first voiceprint cluster was generated) and current time information (time information at which the user recognition command was received), the processor may lower a misrecognition rate despite the changed user voice.

If user recognition is successful, the processor 120 may update the second voiceprint cluster based on the received user's utterance. Meanwhile, that user recognition is successful may mean that the received utterance is the voice of an authorized user. The newly generated second voiceprint cluster is simply changed based on the time information (difference value) of the pre-stored first voiceprint cluster, and thus the latest voice of an actual authorized user may not be reflected. Accordingly, the processor 120 may need an update operation reflecting the user's recent voice. Accordingly, if user recognition is successful, the second voiceprint cluster may be updated based on the received utterance. Since the electronic apparatus 100 updates the voiceprint cluster by reflecting not only the time information but also the recent user voice, the misrecognition rate may be further lowered.

If user recognition is successful, the processor 120 may receive at least one of user activity information or user body information from an external device, and update the second voiceprint based on at least one of the received user activity information or user body information.

The external device may refer to an electronic apparatus including a sensor that senses various types of information. For example, the external device may be a smart watch. The external device may obtain the user's activity information or the user's body information through a sensor. In addition, the external device may transmit at least one of the acquired activity information or body information to the electronic apparatus 100. In addition, the processor 120 may update the second voiceprint cluster based on the received information.

If the user recognition fails, the processor 120 may validate the user's authority, and if the user's authority is validated, the processor 120 may identify the user's health status based on the received user's utterance, and update the second voiceprint cluster based on the user's health status.

The failure of user recognition may mean that the user who spoke the voice is a person who has not been pre-registered. Therefore, in general, if user recognition fails, the processor 120 may deny access to the user who uttered a voice to the electronic apparatus 100. However, when the user voice is changed, user recognition through voice may fail. For example, there may be a situation where the user's body condition is bad and the user may get a frog in his/her neck. The electronic apparatus 100 may update the second voiceprint cluster by additionally considering the situation.

Specifically, if the user recognition fails, the processor 120 may request the user who has additionally uttered a voice to validate user authority. The user authority verification may be a separate authentication method. For example, the user authority verification may be at least one of ID and password input, public certificate, mobile phone text authentication, resident registration card scan, and fingerprint recognition.

In addition, if the user authority is validated by the additional verification after the user recognition fails, the processor 120 may identify the user's health status based on the received user's utterance. In addition, the second voiceprint cluster may be updated based on the identified health status of the user.

Meanwhile, the processor 120 may receive the user's utterance, acquire a voice feature from the received utterance, and if the acquired voice feature does not match at least one pre-registered voiceprint and at least one changed voiceprint, it may be decided that the user recognition has failed and, if the user's authority is validated, the second voiceprint cluster (or cluster) is updated based on the acquired voice feature and based on the updated second voiceprint cluster, the processor 120 may perform user recognition.

The processor 120 may receive the user's utterance through a microphone (not shown) of the electronic apparatus 100. According to another implementation, the electronic apparatus 100 may receive voice data corresponding to the user's utterance acquired from the external device.

The processor 120 may acquire a voice feature from the received utterance. Specifically, the processor 120 may acquire a voice feature from audio data corresponding to the utterance in a predetermined manner. The voice feature may refer to feature information for determining whether the utterance corresponds to a specific user.

The processor 120 may perform a user recognition operation based on the acquired voice feature. Specifically, the processor 120 may identify whether the user is recognized as a pre-stored user based on the user's utterance. The processor 120 may identify whether the voice feature acquired from the utterance matches at least one voiceprint pre-registered in the memory 110. If the acquired voice feature matches at least one pre-registered voiceprint, the processor 120 may identify that user recognition has been successful. In addition, if the acquired voice feature does not match at least one pre-registered voiceprint and at least one changed voiceprint, the processor 120 may identify that user recognition has failed.

If it is identified that user recognition has failed, the processor 120 may validate the user authority separately from the user recognition operation. The processor 120 may validate user authority according to a predetermined method.

Since the operation of validating the user's authority corresponds to the same effect as the user recognition operation, it may correspond to a different type of user recognition operation.

According to an embodiment, the processor 120 may validate the user's authority using the utterance.

Meanwhile, the processor 120 may identify a context corresponding to the acquired voice feature, identify a voice template corresponding to the identified context. If the acquired voice feature does not match the pre-registered at least one voiceprint and the changed at least one voiceprint, the processor 120 may validate the user's authority, and if the user's authority is validated, the processor 120 may obtain cluster configuration information including a center value and a threshold value based on the obtained voice feature, the identified context, the identified voice template or cluster configuration information including a center value and a threshold value based on at least one of a voiceprint corresponding to the user among at least one pre-registered voiceprint, and may update the second voiceprint cluster based on the obtained cluster configuration information.

The processor 120 may identify a context corresponding to the voice feature. The context may include at least one of intoxication, ill state, tired state, wake-up state, shout, murmur, whisper, agitated, throat-choked state, crooning, animated state, comical state.

The processor 120 may identify a voice template corresponding to the identified context. The voice template may refer to voice sample data spoken by the user in various situations. For example, a voice template may refer to at least one of intoxication, ill state, tired state, wake-up state, shout, murmur, whisper, agitated, throat-choked state, crooning, animated state, comical state. The electronic apparauts 100 may store voice templates (or voice sample data or voice data) corresponding, to various contexts corresponding to the user.

The voice template may be different from the voiceprint. The voiceprint may be registered based on a specific utterance for registration among all the utterances of the user. However, the voice template may correspond to all utterances of the user. Accordingly, the voice template may be data that is auxiliarly used when user recognition through the voiceprint fails.

In the operation of validating user authority, the processor 120 may identify a context corresponding to the utterance and a voice template corresponding to the context. In addition, the processor 120 may identify whether the acquired speech feature matches the identified speech template. And, if the acquired voice feature matches the identified voice template, the processor 120 may validate that the user corresponding to the utterance has authority. If the acquired voice feature does not match the identified voice template, it may be validated that the user corresponding to the utterance does not have authority.

If it is identified that there is the user authority, the processor 120 may obtain cluster configuration information based on information related to the utterance. The information related to the utterance may include at least one of an acquired voice feature, an identified context, an identified voice template, or a voiceprint corresponding to a user among at least one pre-registered voiceprint. The cluster configuration information may include a center value (or center point) of a cluster for defining a range of the cluster and a threshold value of the cluster. According to an embodiment, the threshold value of the cluster may refer to a distance value from the center value of the cluster to a voiceprint that is furthest from among the voiceprints included in the cluster. According to another embodiment, the threshold value of the cluster may refer to a predetermined distance value that may include a voiceprint that is furthest from the center value of the cluster among voiceprints included in the cluster.

When the user's authority is validated, the processor 120 may update the second voiceprint cluster so that user recognition of the utterance does not fail in the next user recognition operation. Specifically, if the user's authority is validated, the processor 120 may generate a new voiceprint based on the voice feature of the utterance, and change at least one of the center value or the threshold value of the existing cluster to include the generated voiceprint. In addition, it is possible to update the existing cluster based on the changed cluster configuration information.

According to another embodiment, the processor 120 may validate the user's authority by using information other than the utterance.

Meanwhile, if the acquired voice feature does not match at least one pre-registered voiceprint and at least one changed voiceprint, the processor 120 may acquire parameters other than the received utterance, and based on the acquired parameters, and may validate the user's authority, and when the user's authority is validated, the processor 120 may acquire cluster configuration information including a center value and a threshold value based on at least one of voiceprint corresponding to the user among the acquired voice feature or at least one pre-registered voiceprint, and update the second voiceprint cluster based on the acquired cluster configuration information.

If the acquired voice feature does not match at least one pre-registered voiceprint and at least one changed voiceprint, the processor 120 may identify that user recognition has failed. In addition, the processor 120 may additionally validate user authority. The processor 120 may validate the user authority using other types of data other than the utterance.

Meanwhile, the parameters (the other type of data other than the utterance) may include operation parameters corresponding to the user's operation performed by the electronic apparatus 100, operation parameters corresponding to the user's operation performed by an external device, and a biometric parameter corresponding to the user or a time parameter for the user to access the electronic apparatus 100.

The operation parameter corresponding to the user's operation performed by the electronic apparatus 100 may refer to a predetermined event acquired through a sensor included in the electronic apparatus 100. For example, the predetermined event may include at least one of an event in which the user enters a password, an event in which the user enters a signature, an event in which the user successfully authenticates through a certificate, an event in which the user enters a specific password release pattern, and an event in which the user makes a specific gesture. When the predetermined event is identified from the electronic apparatus 100, the processor 120 may identify that the user has authority.

The operation parameter corresponding to the user's operation performed in the external device may refer to a predetermined event acquired through a sensor included in the external device. The predetermined event may be the same as the operation parameter corresponding to the user's operation performed by the electronic apparatus 100. However, each event may be implemented in a form that is received through an external device other than the electronic apparatus 100. When the predetermined event is identified in the external device, the processor 120 may identify that the user is authorized.

The biometric parameter corresponding to the user may refer to biometric information of the user received by the electronic apparatus 100 or an external device. For example, the biometric information may include at least one of body temperature, blood pressure, and heart rate of the user. When the measured biometric information of the user matches the predetermined biometric information, the processor 120 may identify that the user is authorized.

The time parameter for the user to access the electronic apparatus 100 may refer to time information at which the electronic apparatus 100 receives the user's utterance. When the time information at which the user's utterance is received matches the predetermined time information, the processor 120 may identify that the user is authorized.

The processor 120 may validate user authority based on at least one of the above-described various parameters.

Meanwhile, it may further include an acoustic sensor for receiving spoken sound spoken by the user, and the processor 120 may classify the received spoken sound into at least one of pitch, tone, decibel, or frequency based on a voice processing criterion of the received utterance.

The processor 120 may obtain a voice feature based on at least one of the classified pitch, tone, decibel, and frequency.

Meanwhile, the processor 120 may obtain a spoken voiceprint corresponding to the utterance based on the acquired voice feature, and obtain a similarity value between the acquired spoken voiceprint and at least one pre-registered voiceprint and the changed at least one voiceprint, and if the obtained similarity value is less than or equal to a threshold value, it may be determined that user recognition has failed, and if the obtained similarity value exceeds the threshold value, it may be determined that the user recognition has been successful, and at least one pre-registered voiceprint is identification voiceprint information, at least one pre-registered voiceprint may be included in the first voiceprint cluster, and the first voiceprint cluster may include cluster configuration information including a predetermined center value and a predetermined threshold value.

The spoken voiceprint may refer to voiceprint data corresponding to a voice spoken by the user. Further, the processor 120 may perform a user recognition operation by comparing the spoken voiceprint with the pre-registered voiceprint. Specifically, it may be possible to determine whether to recognize the user by obtaining a similarity value between the spoken voiceprint and the pre-registered voiceprint. For example, when the similarity value exceeds the threshold value, the processor 120 may determine that user recognition is successful.

The electronic apparatus 100 may store a plurality of voiceprint clusters. One of the plurality of voiceprint clusters may include the plurality of voiceprints. Each user may include at least one voiceprint cluster. According to an implementation example, two or more voiceprint clusters may be registered to one user.

Meanwhile, if the acquired voice feature does not match at least one pre-registered voiceprint and at least one changed voiceprint, the processor 120 may validate the user authority based on sensing data obtained from a sensor or input data obtained through a user interface.

If the acquired voice feature does not match at least one pre-registered voiceprint and at least one changed voiceprint, the processor 120 may determine that user recognition has failed, and may validate the user authority through an auxiliary means.

According to an embodiment, the processor 120 may validate the user authority based on sensing data obtained from a sensor. Specifically, the processor 120 may acquire sensing data through a sensor included in the electronic apparatus 100 or an external device, and if the sensing data corresponds to a predetermined event, the processor 120 may identify that the user has authority. The sensor may be at least one of a camera, a biometric sensor, an illuminance sensor, an acoustic sensor, or a 3D sensor.

According to another embodiment, the processor 120 may validate the user authority based on input data acquired through a user interface. The user interface may refer to an operation inputter, and may refer to one of a button or a touch pad for receiving the user's specific input. When the user inputs a predetermined event through the user interface, the processor 120 may identify that the user has authority.

Meanwhile, the memory 110 may store at least one voice variability identifier (cluster ID) including at least one voice template, and the processor 120 may obtain utterance corresponding to an utterance based on the acquired voice feature, and identify a voice variability identifier corresponding to the voice variability identifier by comparing the obtained speech voiceprint with at least one speech template, and identify a context corresponding to the utterance based on the identified voice variability identifier, and include at least one of status of intoxication, ill state, tired state, wake-up state, shout, murmur, whisper, agitated, throat-choked state, crooning, animated state, comical state.

The electronic apparatus 100 may store at least one cluster corresponding to the user, and each cluster may include cluster identification information (ID) (voice variability identifier) for specifying clusters. Accordingly, the processor 120 may identify a cluster that does not match with the utterance but includes a voiceprint that is most similar to the utterance. Further, the processor 120 may identify a context corresponding to the utterance (or utterance) based on the identified cluster. Further, the processor 120 may validate the user authority based on the utterance and the identified context.

Meanwhile, the processor 120 may acquire an embedding value by embedding the utterance in a predetermined method, and a difference value between the acquired embedding value and a first center value of a first voiceprint cluster exceeds a first threshold value, and if a difference value between the obtained embedding value and a second center value of a second voiceprint cluster exceeds a second threshold value, it may be determined that user recognition has failed. In addition, the processor 120 may additionally validate the user authority.

The embedding may refer to an operation of converting data in order to compare data at the same level. Specifically, the processor 120 may convert (or embed) the utterance in a predetermined manner so as to compare how far apart the utterance is from the center value of the existing cluster. In addition, the processor 120 may obtain a first center value and a first threshold value of a cluster corresponding to the user, a comparison criterion. In addition, the processor 120 may obtain a distance value (or difference value) between a transformed value (or embedding value) and the first center value of the cluster corresponding to the user. In addition, the processor 120 may identify whether the obtained distance value (or difference value) exceeds the first threshold value. If the obtained distance value (or difference value) exceeds the first threshold value, the processor 120 may determine that user recognition has failed. If the acquired distance value (or difference value) is less than the first threshold value, the processor 120 may determine that user recognition is successful.

Meanwhile, when the user authority is validated, the processor 120 may obtain a third center value and a third threshold value corresponding to the utterance, and may obtain cluster configuration information including a fourth center value and a fourth threshold value based on the first center value, the first threshold value, the second center value, and the second center value, the third center value, the third threshold value, and update the second voiceprint cluster based on the obtained cluster configuration information.

If necessary, the processor 120 may obtain the fourth center value and the fourth threshold value by omitting information on the first voiceprint cluster (first center value and first threshold value).

When the user authority is validated, the processor 120 may identify the second voiceprint cluster corresponding to the validated user, and obtain a second center value and a second threshold value, which are configuration information of the identified second voiceprint cluster. In addition, the processor 120 may obtain a third center value and a third threshold value corresponding to the utterance based on the utterance. For example, if there are a plurality of utterances, the processor 120 may obtain a third center value that is average location information based on location information of the plurality of utterances. In addition, the processor 120 may identify the utterance which is furthest from the third center value among the plurality of utterances, and obtain distance information from the third center value to the furthest utterances as a third threshold. In addition, the processor 120 may obtain a fourth center value and a fourth threshold value based on the second cluster configuration information (second center value and second threshold value) and information corresponding to the utterance (third center value and third threshold value). In addition, the existing cluster information may be changed using the obtained fourth center value and the obtained fourth threshold value. Specifically, the processor may change (or update) from the second center value and the second threshold value to the fourth center value and the fourth threshold value among the configuration information of the second voiceprint cluster.

Meanwhile, if a difference value between the acquired embedding value and the first central value of the first voiceprint cluster exceeds the fifth threshold, and a difference value between the acquired embedding value and the second center value of the second voiceprint cluster exceeds the fifth threshold value, the processor 120 may generate a third voiceprint cluster based on the obtained third center value and the third threshold, and additionally register the third voiceprint cluster generated in the voiceprint cluster corresponding to the user.

The processor 120 may generate a new cluster without changing the existing cluster when the existing cluster (the first voiceprint cluster and the second voiceprint cluster) and the acquired embedding value exceed the fifth threshold. In addition, the processor 120 may add a cluster generated in the cluster corresponding to the user.

Figure 18:
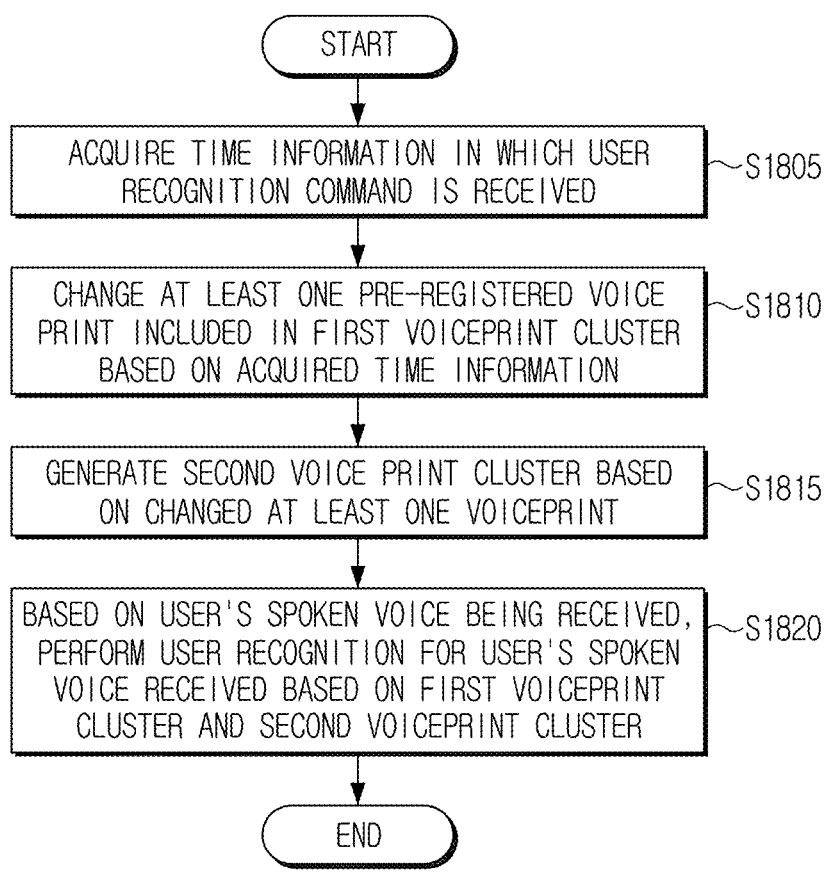
FIG. 18 is a flowchart illustrating a method of controlling an electronic apparatus according to an embodiment of the present disclosure.

FIG. 18 is a flowchart illustrating a control method for an electronic apparatus according to an embodiment of the disclosure.

Referring to FIG. 18, when a user recognition command is received, a control method of the electronic apparatus 100 for storing at least one pre-registered voiceprint and a first voiceprint cluster including at least one pre-registered voiceprint according to an embodiment of the disclosure includes acquiring time information at which the user recognition command is received (S1805), changing at least one pre-registered voiceprint included in the first voiceprint cluster based on the acquired time information (S1810), generating a second voiceprint cluster based on the changed at least one voiceprint (S1815), and performing user recognition of the received user's utterance based on the first voiceprint cluster and the second voiceprint cluster when the user's utterance is received (S1820).

The control method may further include updating the second voiceprint cluster based on the received user's uttered voice, if user recognition is successful.

The control method may further include receiving at least one of user activity information or user body information from an external device when the user recognition is successful, and updating the second voiceprint cluster based on at least one of the received user activity information or user body information.

The control method may further include validating the user authority when user recognition fails, identifying the user's health status based on the received user's utterance when the user authority is validated, and updating the second voiceprint cluster based on the identified user's health status.

The control method may further include acquiring a voice feature from the received utterance, and if the acquired voice feature does not match at least one pre-registered voiceprint and at least one changed voiceprint, determining that the user recognition has failed and validating user authority, and if the user authority is validated, updating the second voiceprint cluster based on the acquired voice feature, and performing user recognition based on the updated second voiceprint cluster.

The control method may further include identifying a context corresponding to the acquired voice feature, identifying a voice template corresponding to the identified context, if the acquired voice feature does not match with at least one pre-registered voiceprint and at least one changed voiceprint, validating the user authority based on the acquired voice feature and the identified voice template, and if the user authority is validated, acquiring configuration information including a center value and a threshold value based on at least one of voiceprints corresponding to the user among the acquired voice feature, the identified context, the identified voice template, or at least one pre-registered voiceprint, and updating the second voiceprint cluster based on the obtained cluster configuration information.

The control method may further include obtaining a parameter other than the received utterance, if the acquired voice feature does not match at least one pre-registered voiceprint and at least one changed voiceprint, and validating user authority based on the acquired parameter, acquiring configuration information including a center value and a threshold value based on at least one of voiceprints corresponding to the user among the acquired voice feature or the pre-registered at least one voiceprint when the user authority is validated, and updating the second voiceprint cluster based on the acquired cluster configuration information.

The parameter may include at least one of an operation parameter corresponding to a user operation performed by the electronic apparatus 100, an operation parameter corresponding to a user operation performed by an external device, a biometric parameter corresponding to the user, or a time parameter in which the user accesses to the electronic apparatus 100.

The control method may further include receiving the utterance uttered by the user and decomposing the received utterance into at least one of pitch, tone, decibel, or frequency based on a voice processing criterion.

The control method may include obtaining an utterance corresponding to the utterance based on the acquired voice feature, obtaining a similarity value between the acquired utterance and at least one pre-registered voiceprint, and at least one changed voiceprint, if the obtained similarity value is less than or equal to a threshold value, determining that user recognition has failed, and if the obtained similarity value exceeds the threshold value, determining that user recognition is successful, wherein the at least one pre-registered voiceprint is user identification information, and at least one pre-registered voiceprint may be included in the first voiceprint cluster, and the first voiceprint cluster may include cluster configuration information including a predetermined center value and a threshold value.

The control method may further include, if the acquired voice feature does not match at least one pre-registered voiceprint and at least one changed voiceprint, validating user authority based on sensing data obtained from a sensor or input data obtained through a user interface.

The electronic apparatus 100 may include storing at least one voice variability identifier (cluster ID) including at least one voice template, wherein the processor is configured to obtain speech voiceprint corresponding to the utterance based on the obtained voice feature, identifying a voice variability identifier corresponding to the speech voiceprint by comparing the obtained speech voiceprint and the at least one voice template, and identifying a context corresponding to the speech voiceprint based on the identified voice variability identifier, and wherein the context may include intoxication, ill state, tired state, wake-up state, shout, murmur, whisper, agitated, throat-choked state, crooning, animated state, comical state.

The method may further include obtaining an embedding value by embedding the speech voiceprint in a predetermined method, and based on a difference value between the obtained embedding value and a first center value of the first voiceprint cluster exceeding a first threshold value, and a difference value between the obtained embedding value and a second center value of the second voiceprint cluster exceeding a second threshold value, determining user recognition is failed and validate the user authority.

The method may further include, based on the user authority being validated, obtaining a third center value and a third threshold value corresponding to the speech voiceprint, obtaining cluster configuration information including a fourth center value and a fourth threshold value based on the first center value, the first threshold value, the second center value, the second threshold value, the third center value, and the third threshold value, updating the second voiceprint cluster based on the obtained cluster configuration information.

The method may include, based on a difference value between the obtained embedding value and the first center value of the first voiceprint cluster exceeding a fifth threshold value, and a difference value between the obtained embedding value and the second center value of the second voiceprint cluster exceeding the fifth threshold value, generating a third voiceprint cluster based on the acquired third center value and the third threshold value, and further registering the generated third voiceprint cluster.

Meanwhile, the method of controlling an electronic apparatus as illustrated in FIG. 18 may be executed on the electronic apparatus having the configuration of FIG. 17, and may be executed on an electronic apparatus having other configurations.

Figure 19:
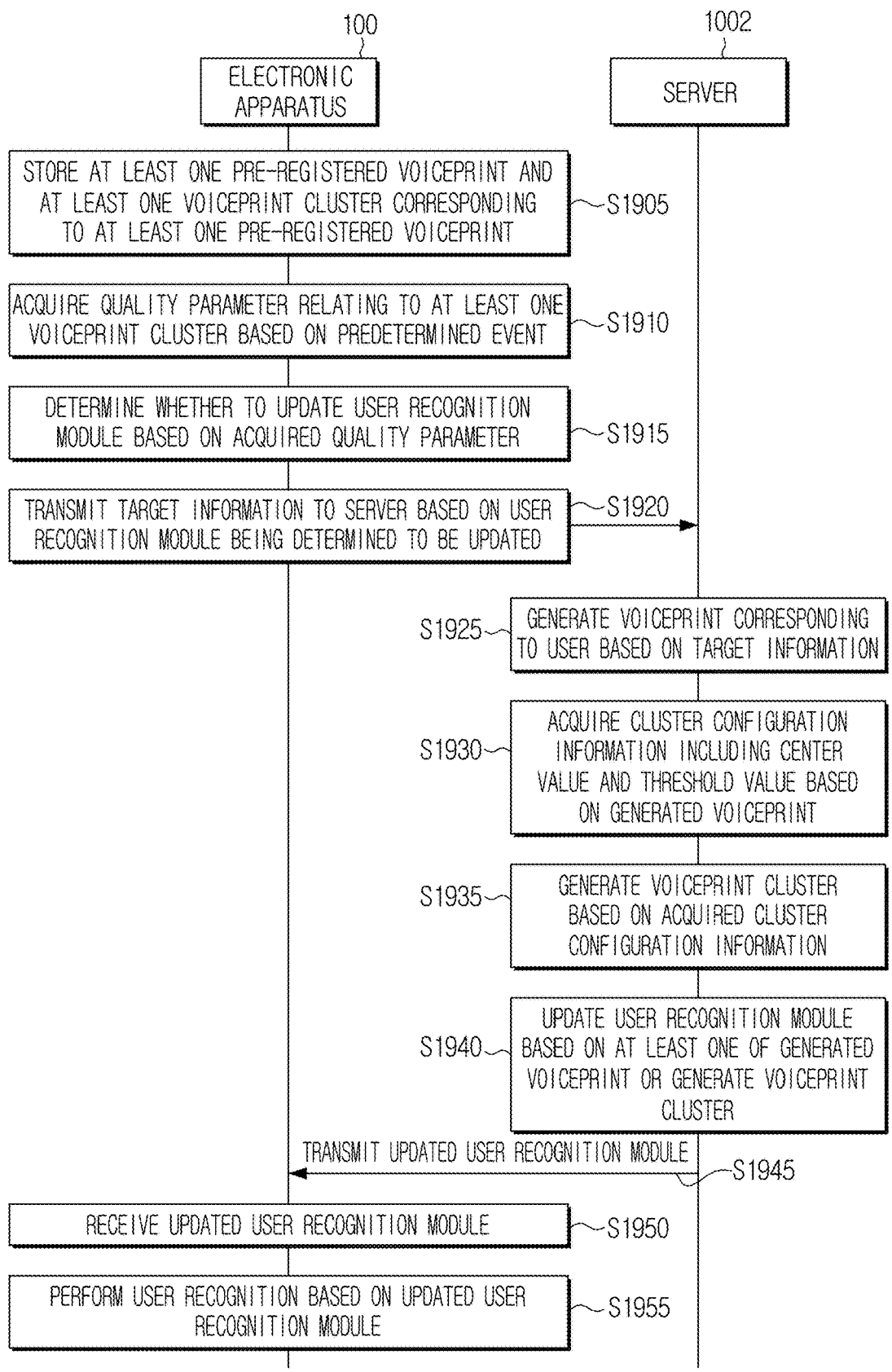
FIG. 19 is a flowchart illustrating a system including an electronic apparatus and a server according to an embodiment of the present disclosure.

FIG. 19 is a flowchart illustrating a system including an electronic apparatus and a server according to an embodiment of the disclosure.

Referring to FIG. 19, a system including the electronic apparatus 100 and a server 1002 according to an embodiment of the disclosure is configured to store at least one pre-registered voiceprint and at least one voiceprint cluster corresponding to at least one pre-registered voiceprint (S1905), obtain a quality parameter regarding at least one voiceprint cluster based on the predetermined event (S1910), determine whether to update user recognition module based on a quality parameter (S1915), when it is determined to update the user recognition module, transmit a target information including at least one of the at least one pre-registered voiceprint, the at least one pre-registered voiceprint cluster, voice feature corresponding to the at least one voiceprint cluster, user identification information, voiceprint cluster attribute information, information on user recognition module, to the server 1002 (S1920), wherein the voiceprint cluster attribute information includes at least one attribute of a fixed cluster or a variable cluster, wherein the server generates a voiceprint corresponding to the user based on target information transmitted from the electronic apparatus 100 (S1925), obtain cluster configuration information including a center value and a threshold value based on the generated voiceprint (S1930), generate a voiceprint cluster based on the obtained cluster configuration information (S1935), update the user recognition module based on at least one of the generated voiceprint or the generated voiceprint cluster (S1940), transmit the updated user recognition module to the electronic apparatus 100 (S1945), and receive user recognition model adapted from the server 1002, and perform user recognition based on the updated user recognition model (S1955).

The predetermined event may refer to an event in which a control command for obtaining a quality parameter is obtained. For example, the control command may be directly input by the user. As another example, the control command may be automatically generated in every predetermined period.

The electronic apparatus 100 may acquire a quality parameter based on the predetermined event. The acquisition operation related to the quality parameter will be described below in FIGS. 20 and 21.

The electronic apparatus 100 may determine to update the user recognition module when the obtained quality parameter corresponds to a predetermined threshold range. Specifically, if the obtained quality parameter is lower than a predetermined threshold, the electronic apparatus 100 may determine to update the user recognition module.

If it is determined to update the user recognition module, target information may be transmitted to an external server. The electronic apparatus 100 may use a communication interface to transmit information to an external server or to receive information from an external server. The target information may include at least one of at least one pre-registered voiceprint, voice feature corresponding to at least one voiceprint cluster, user identification information, voiceprint cluster attribute information, information on user identification module.

The voiceprint corresponding to the user may refer to an utterance.

The operations S1925 to S1940 may correspond to the operation S1820 of FIG. 18. Accordingly, the operations described in FIGS. 18 to 19 may be equally applied.

The electronic apparatus 100 may obtain a center value corresponding to one of at least one pre-registered voiceprint cluster. The electronic apparatus 100 may obtain an average value of voiceprint distance between at least one voiceprint included in one cluster (refer to the embodiment 2010 of FIG. 20). The electronic apparatus 100 may obtain a minimum distance value (refer to the equation 2105 of FIG. 21) from among cluster distance values (refer to the embodiment 2020 of FIG. 20) of each of one cluster and the remaining clusters. In addition, the electronic apparatus 100 may obtain a quality parameter based on at least one of an acquired center value, an acquired distance average value, or an acquired minimum distance value.

The server 1002 may generate a cluster map based on the generated voiceprint cluster, and may update the user recognition module based on the generated cluster map.

The cluster map may refer to information for synthesizing a plurality of clusters.

The server 1002 may delete at least one of at least one pre-registered voiceprint cluster among target information received from the electronic apparatus 100, and generate a voiceprint corresponding to the user based on voice features corresponding to the deleted voiceprint cluster, obtain cluster configuration information including a center value and a threshold based on the generated voiceprint, and generate voiceprint cluster based on the obtained cluster configuration information.

The server 1002 may receive target information from each of the plurality of electronic apparatuses 100 and shortlist at least one user recognition module based on pre-stored listing information among the plurality of user recognition modules received from each of the plurality of electronic apparatus, and wherein the pre-stored listing information may include at least one of a predetermined area or a predetermined category.

Figure 20:
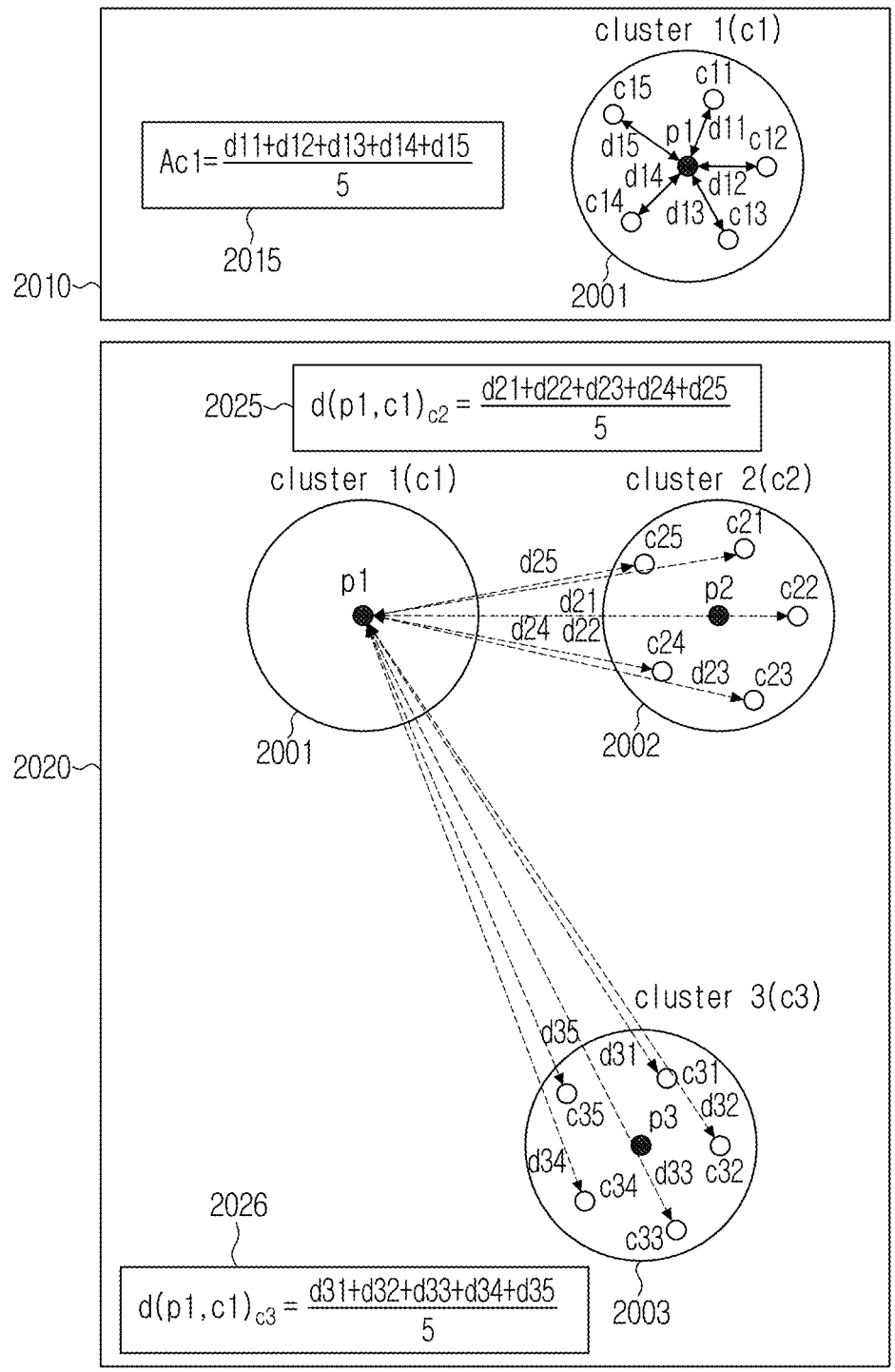
FIG. 20 is a view illustrating a calculation process used to obtain a quality parameter corresponding to a cluster.

FIG. 20 is a view illustrating a calculation process used to obtain a quality parameter corresponding to a cluster.

Referring to FIG. 20, the electronic apparatus 100 in an embodiment 2010 may obtain a center value $p1$ of a first cluster 2001 from among configuration information of the first cluster 2001. In addition, the first cluster 2001 may include a plurality of voiceprints $c11$, $c12$, $c13$, $c14$, and $c15$. In addition, the electronic apparatus 100 may obtain distance information $d11$, $d12$, $d13$, $d14$, and $d15$ of each voiceprint from the center value $p1$ of the first cluster 2001. For example, a distance from the center value $p1$ of the first cluster 2001 to the voiceprint $c11$ may be $d11$, a distance from the center value $p1$ of the first cluster 2001 to the voiceprint $c12$ may be $d12$, a distance from the center value $p1$ of the first cluster 2001 to the voiceprint $c13$ may be $d13$, a distance from the center value $p1$ of the first cluster 2001 to the voiceprint $c14$ may be $d14$, and a distance from the center value $p1$ of the first cluster 2001 to the voiceprint $c1$ may be $d15$.

In addition, the electronic apparatus 100 may obtain an average value of the distance from the center value $p1$ of the first cluster 2001 to each voiceprint based on equation 2015. Specifically, the average distance value $Ac1$ may be $(d11+d12+d13+d14+d15)/5$.

In another embodiment 2020, the electronic apparatus 100 may obtain a distance value to the other cluster based on the first cluster 2001. The other cluster may be at least one other cluster, and it is assumed that there are two different clusters 2002 and 2003 in the embodiment 2020.

It is assumed that the second cluster 2002 includes a plurality of voiceprints c21, c22, c23, c24, c25, and the third cluster 2003 includes the plurality of voiceprints c31, c32, c33, c34, c35.

The electronic apparatus 100 may obtain a distance value between the cluster and the cluster. For example, a distance value between the clusters may be obtained based on a center value of each cluster. As another example, a distance value between the clusters may be obtained based on an average value of distances from a center value of a reference cluster to voiceprints included in the other cluster.

Another embodiment 2020 is to describe a method of obtaining a distance value according to the second method.

In addition, it is assumed that a distance from the center value p1 of the first cluster 2001 to the voiceprint c21 included in the second cluster 2002 may be d21, a distance from the center value p1 of the first cluster 2001 to the voiceprint c22 included in the second cluster 2002 may be d22, a distance from the center value p1 of the first cluster 2001 to the voiceprint c23 included in the second cluster 2002 may be d23, a distance from the center value p1 of the first cluster 2001 to the voiceprint c24 included in the second cluster 2002 may be d24, and a distance from the center value p1 of the first cluster 2001 to the voiceprint c25 included in the second cluster 2002 may be d25.

In addition, it is assumed that a distance from the center value p1 of the first cluster 2001 to the voiceprint c31 included in the third cluster 2003 may be d31, a distance from the center value p1 of the first cluster 2001 to the voiceprint c32 included in the third cluster 2003 may be d32, a distance from the center value p1 of the first cluster 2001 to the voiceprint c33 included in the third cluster 2003 may be d33, a distance from the center value p1 of the first cluster 2001 to the voiceprint c34 included in the third cluster 2003 may be d34, a distance from the center value p1 of the first cluster 2001 to the voiceprint c35 included in the third cluster 2003 may be d35.

Meanwhile, the electronic apparatus 100 may obtain distance values of the first cluster 2001 and the second cluster 2002 based on equation 2025. Specifically, the electronic apparatus 100 may obtain an average value of the distance from the center value p1 of the first cluster 2001 to each voiceprint included in the second cluster 2002 based on the equation 2025. An average distance $(d(p1,c1)_{c2})$ from the center value p1 of the first cluster 2001 to each voiceprint included in the second cluster 2002 may be (d21+d22+d23+d24+d25)/5.

Meanwhile, the electronic apparatus 100 may obtain distance values of the first cluster 2001 and the third cluster 2003 based on equation 2026. Specifically, the electronic apparatus 100 may obtain an average value of the distance from the center value p1 of the first cluster 2001 to each voiceprint included in the third cluster 2003 based on the equation 2026. The average distance $(d(p1, c1)_{c3})$ from the center value p1 of the first cluster 2001 to each voiceprint included in the third cluster 2003 may be (d31+d32+d33+d34+d35)/5.

FIG. 21 is a view illustrating a calculation process used to obtain a quality parameter corresponding to a cluster.

Referring to FIG. 21, the electronic apparatus 100 may identify a cluster closest to the first cluster 2001 based on equation 2105. As the assumption of FIG. 20, it is assumed that clusters different from the first cluster 2001 are the second cluster 2002 and the third cluster 2003.

In order to identify the cluster closest to the first cluster 2001, the electronic apparatus 100 may obtain a distance value for each of the first cluster 2001 and the other clusters. A distance value between clusters may be obtained through the embodiment 2020 of FIG. 20. Specifically, a distance value Bi to the closest cluster based on a cluster ci may be min $d(p, ci)_{cj}$. The cj may refer to a cluster other than the reference cluster ci.

It is assumed that there are two different clusters in the embodiment 2020 of FIG. 20. The distance value B1 to the closest cluster based on the first cluster may be min {d(p1, c1)$_{c2}$, d(p1,c1)$_{c3}$)}. The d(p1,c1)$_{c2}$ may be an average value of the distance from the center value p1 of the first cluster 2001 to the voiceprint included in the second cluster 2002, and d(p1,c1)$_{c3}$ may be an average value of the distance from the center value p1 of one cluster 2001 to the voiceprints included in the third cluster 2003.

As illustrated in FIG. 20, the average distance from the center value p1 of the first cluster 2001 to the voiceprint included in the second cluster 2002 may be less than the average value of the distance from the center value p1 of the first cluster 2001 to the average value of the distance of the voiceprint included in the third cluster 2003. The electronic apparatus 100 may obtain a distance value from the first cluster 2001 to the closest cluster as d(p1, c1)$_{c2}$.

Meanwhile, the electronic apparatus 100 may obtain the quality parameter of the cluster ci based on equation 2110. Specifically, the quality parameter Qci of the cluster ci may be (Bi−Aci)/(max{Bi,Aci}).

When applied to the embodiment 2020 of FIG. 20, a quality index Qc1 for the first cluster 2001 may be (d(p1, c1)$_{c2}$−Ac1)/(max(d(p1,c1)$_{c2}$, Ac1)}).

The d(p1,c1)$_{c2}$ may be an average value of the distance from the center value p1 of the first cluster 2001 to the voiceprints included in the second cluster 2002, and Ac1 may be an average value of the first cluster 2001 from the center value p1 of the first cluster 2001 to the average value of the distance to the voiceprint included in the first cluster 2001.

According to the embodiment 2020 of FIG. 20, it is assumed that the average distance from the center value p1 of the first cluster 2001 to the voiceprints included in the first cluster 2001 is smaller than the average distance from the center value p1 of the first cluster 2001 to the voiceprints included in the second cluster 2002. The electronic apparatus 100 may finally obtain the quality index Qc1 for the first cluster 2001 as (d(p1,c1)$_{c2}$−Ac1)/(d(p1,c1)$_{c2}$).

As the average value Ac1 of the distance from the center value p1 of the first cluster 2001 to the voiceprints included in the first cluster 2001 decreases (closer to 0), the quality index Qc1 of the first cluster 2001 may be close to 1.

In addition, as the average value Ac1 of the distance from the center value p1 of the first cluster 2001 to the voiceprints included in the first cluster 2001 increases, the quality index Qc1 of the first cluster 2001 may be close to 0.

The meaning that the average distance value Ac1 of the distance from the center value p1 of the first cluster 2001 to the voiceprints included in the first cluster 2001 increases may indicate that the distance from the center value p1 of the first cluster 2001 to the voiceprints included in the second cluster 2002 becomes closer to the average value.

Therefore, the closer the quality index for the cluster is to 1, the denser the voiceprints included in the cluster may be. The electronic apparatus 100 may identify that the closer the quality index for a particular cluster is to 1, the better the quality.

Also, if the quality index for a particular cluster is smaller than a predetermined threshold value, the electronic apparatus 100 may identify that the quality for the particular cluster is not good and determine to update the user recognition module.

Meanwhile, the methods according to various embodiments of the disclosure described above may be implemented in an application form that can be installed in an existing electronic apparatus.

The above-described methods according to various embodiments of the disclosure may be implemented only by software upgrade or hardware upgrade of an existing electronic apparatus.

Also, the various embodiments of the disclosure described above may be performed through an embedded server provided in an electronic apparatus or an external server of at least one of an electronic apparatus and a display device.

According to an embodiment of the disclosure, the various embodiments described above may be implemented as software including instructions stored in a machine-readable storage media which is readable by a machine (e.g., a computer). The device may include the electronic device according to the disclosed embodiments, as a device which calls the stored instructions from the storage media and which is operable according to the called instructions. When the instructions are executed by a processor, the processor may directly perform functions corresponding to the instructions using other components or the functions may be performed under a control of the processor. The instructions may include codes generated or executed by a compiler or an interpreter. The machine-readable storage media may be provided in a form of a non-transitory storage medium. The 'non-transitory' means that the storage medium does not include a signal and is tangible, but does not distinguish whether data is stored semi-permanently or temporarily in the storage medium.

The computer program product may be distributed in a form of the machine-readable storage media (e.g., compact disc read only memory (CD-ROM) or distributed online through an application store (e.g., PlayStore™). In a case of the online distribution, at least a portion of the computer program product may be at least temporarily stored or provisionally generated on the storage media, such as a manufacturer's server, the application store's server, or a memory in a relay server.

According to various embodiments, each of the elements (e.g., a module or a program) of the above-described elements may be comprised of a single entity or a plurality of entities. According to various embodiments, one or more elements of the above-described corresponding elements or operations may be omitted, or one or more other elements or operations may be further included. Alternatively or additionally, a plurality of elements (e.g., modules or programs) may be integrated into one entity. In this case, the integrated element may perform one or more functions of the element of each of the plurality of elements in the same or similar manner as being performed by the respective element of the plurality of elements prior to integration. According to various embodiments, the operations performed by a module, program, or other elements may be performed sequentially, in a parallel, repetitively, or in a heuristically manner, or one or more of the operations may be performed in a different order, omitted, or one or more other operations may be further included.

While the present disclosure has been shown and described with reference to various embodiments thereof, but the disclosure is not limited to the specific embodiments described above, and is generally in the technical field belonging to the disclosure without departing from the scope of the disclosure claimed in the claims. Various modifications can be implemented by those skilled in the art, these modifications should not be individually understood from the technical idea, or perspective of the disclosure.

What is claimed is:

1. An electronic apparatus comprising:
   a memory configured to store a first voiceprint cluster including a plurality of pre-registered voiceprints and information of time at which the first voiceprint cluster is generated; and
   a processor configured to:
   based on a user recognition command being received, obtain information of time at which the user recognition command is received,
   change at least one pre-registered voiceprint of the plurality of pre-registered voiceprints included in the first voiceprint cluster based on a difference value between the obtained information of time at which the user recognition command is received and the stored information of time at which the first voiceprint cluster is generated,
   generate a second voiceprint cluster based on the changed at least one pre-registered voiceprint, and
   based on an utterance of a user being received, perform user recognition with respect to the received utterance based on the first voiceprint cluster and the second voiceprint cluster.

2. The electronic apparatus of claim 1, wherein the processor is configured to, based on the user recognition being successful, update the second voiceprint cluster based on the received utterance.

3. The electronic apparatus of claim 2, wherein the processor is configured to validate an authority of the user based on failure of the user recognition,
   based on the authority being validated, identify health status of the user based on the received utterance, and
   update the second voiceprint cluster based on the identified health status.

4. The electronic apparatus of claim 1, wherein the processor is configured to, based on the user recognition being successful, receive at least one of user activity information or user body information from an external device, and
   update the second voiceprint cluster based on the received at least one of user activity information or user body information.

5. The electronic apparatus of claim 1, wherein the processor is configured to obtain voice feature from the received utterance,
   based on a mismatch between the obtained voice feature and the at least one pre-registered voiceprint and the changed at least one pre-registered voiceprint, determine the user recognition as failure and validate an authority of the user,
   based on the authority being validated, update the second voiceprint cluster based on the obtained voice feature, and
   perform user recognition based on the updated second voiceprint cluster.

6. The electronic apparatus of claim 5, wherein the processor is configured to identify a context corresponding to the obtained voice feature,
   identify a voice template corresponding to the identified context, based on a mismatch between the obtained voice feature and the at least one pre-registered voiceprint and the changed at least one pre-registered voiceprint, validate the authority based on the obtained voice feature and the identified voice template, based on the authority being validated, obtain cluster configuration information including a center value and a threshold value based on at least one of a voiceprint corresponding to the user among the obtained voice feature, the identified context, the identified voice template or the at least one pre-registered voiceprint, and update the second voiceprint cluster based on the obtained cluster configuration information.

7. The electronic apparatus of claim 5, wherein the processor is configured to obtain a parameter other than the received utterance based on the mismatch between the obtained voice feature and the at least one pre-registered voiceprint and the changed at least one pre-registered voiceprint, validate the authority based on the obtained parameter, based on the authority being validated, obtain cluster configuration information including a center value and a threshold value based on at least one of a voiceprint corresponding to the user among the obtained voice feature or the at least one pre-registered voiceprint, and update the second voiceprint cluster based on the obtained cluster configuration information.

8. The electronic apparatus of claim 7, wherein the parameter includes at least one of an operation parameter corresponding to a user operation performed on the electronic apparatus, an operation parameter corresponding to the user operation performed on an external device, a biometric parameter corresponding to the user, or a time parameter for the user to access the electronic apparatus.

9. The electronic apparatus of claim 5, wherein the processor is configured to obtain an utterance voiceprint corresponding to the utterance based on the obtained voice feature, obtain a similarity value between the obtained utterance voiceprint, and the at least one pre-registered voiceprint and the changed at least one pre-registered voiceprint, based on the obtained similarity value being smaller than a threshold value, determine failure of the user recognition, and based on the obtained similarity value exceeding the threshold value, determine that the user recognition is successful, wherein the at least one pre-registered voiceprint is user identification information, wherein the at least one pre-registered voiceprint is included in the first voiceprint cluster, and wherein the first voiceprint cluster includes cluster configuration information including a predetermined center value and a predetermined threshold value.

10. The electronic apparatus of claim 5, wherein the processor is configured to, based on the mismatch between the obtained voice feature, and the at least one pre-registered voiceprint and the changed at least one pre-registered voiceprint, validate the authority based on sensing data obtained from a sensor or input data obtained through a user interface.

11. The electronic apparatus of claim 5, wherein the memory is configured to store at least one voice variability identifier (cluster ID) including at least one voice template, wherein the processor is configured to obtain utterance voiceprint corresponding to the utterance based on the obtained voice feature, identify a voice variability identifier corresponding to the utterance voiceprint by comparing the obtained utterance voiceprint and the at least one voice template, and identify a context corresponding to the utterance voiceprint based on the identified voice variability identifier, wherein the context includes at least one of intoxication, ill state, tired state, wake-up state, shout, murmur, whisper, agitated, throat-choked state, crooning, animated state, comical state.

12. The electronic apparatus of claim 11, wherein the processor is configured to obtain an embedding value by embedding the utterance voiceprint in a predetermined method, and based on a difference value between the obtained embedding value and a first center value of the first voiceprint cluster exceeding a first threshold value, and a difference value between the obtained embedding value and a second center value of the second voiceprint cluster exceeding a second threshold value, determine that user recognition is failed and validate the authority of the user.

13. The electronic apparatus of claim 12, wherein the processor is configured to, based on the authority being validated, obtain a third center value and a third threshold value corresponding to the utterance voiceprint, obtain cluster configuration information including a fourth center value and a fourth threshold value based on the first center value, the first threshold value, the second center value, the second threshold value, the third center value, and the third threshold value, and update the second voiceprint cluster based on the obtained cluster configuration information.

14. The electronic apparatus of claim 13, wherein the processor is configured to, based on the difference value between the obtained embedding value and the first center value of the first voiceprint cluster exceeding a fifth threshold value, and the difference value between the obtained embedding value and the second center value of the second voiceprint cluster exceeding the fifth threshold value, generate a third voiceprint cluster based on the third center value and the third threshold value, and further register the generated third voiceprint cluster.

15. The electronic apparatus of claim 1, wherein the processor is further configured to obtain the difference value between the obtained information of time at which the user recognition command is received and the stored information of time at which the first voiceprint cluster is generated.

16. A method of controlling an electronic apparatus that stores a first voiceprint cluster including a plurality of pre-registered voiceprints and information of time at which the first voiceprint cluster is generated, the method comprising:

based on a user recognition command being received, obtaining information of time at which the user recognition command is received;

changing at least one pre-registered voiceprint of the plurality of pre-registered voiceprints included in the first voiceprint cluster based on a difference value between the obtained information of time at which the user recognition command is received and the stored information of time at which the first voiceprint cluster is generated;

generating a second voiceprint cluster based on the changed at least one pre-registered voiceprint; and based on an utterance of a user being received, performing user recognition with respect to the received utterance based on the first voiceprint cluster and the second voiceprint cluster.

17. The method of claim 16, further comprising, based on the user recognition being successful, updating the second voiceprint cluster based on the received utterance.

18. The method of claim 16, further comprising:
based on the user recognition being successful, receiving at least one of user activity information or user body information from an external device; and
updating the second voiceprint cluster based on the received at least one of user activity information or user body information.

19. The method of claim 17, further comprising:
validating an authority of the user based on failure of the user recognition;
based on the authority being validated, identifying a health status of the user based on the received utterance; and
updating the second voiceprint cluster based on the identified health status.

20. The method of claim 16, further comprising:
obtaining a voice feature from the received utterance;
based on a mismatch between the obtained voice feature and the at least one pre-registered voiceprint and the changed at least one pre-registered voiceprint, determining the user recognition as failure and validating an authority of the user;
based on the authority being validated, updating the second voiceprint cluster based on the obtained voice feature; and
performing user recognition based on the updated second voiceprint cluster.

21. The method of claim 16, wherein the changing of the at least one pre-registered voiceprint comprises obtaining the difference value between the obtained information of time at which the user recognition command is received and the stored information of time at which the first voiceprint cluster is generated.

22. A computer program product comprising a non-transitory computer-readable recording medium having recording thereon a program for performing a control method of an electronic apparatus that stores a first voiceprint cluster including a plurality of pre-registered voiceprints and information of time at which the first voiceprint cluster is generated, the method comprising:
based on a user recognition command being received, obtaining information of time at which the user recognition command is received;
changing at least one pre-registered voiceprint of the plurality of pre-registered voiceprints included in the first voiceprint cluster based on a difference value between the obtained information of time at which the user recognition command is received and the stored information of time at which the first voiceprint cluster is generated;
generating a second voiceprint cluster based on the changed at least one pre-registered voiceprint; and
based on an utterance of a user being received, performing user recognition with respect to the received utterance based on the first voiceprint cluster and the second voiceprint cluster.

23. The computer program product of claim 22, wherein the changing of the at least one pre-registered voiceprint comprises obtaining the difference value between the obtained information of time at which the user recognition command is received and the stored information of time at which the first voiceprint cluster is generated.

* * * * *